(12) United States Patent
Chan et al.

(10) Patent No.: US 7,845,039 B2
(45) Date of Patent: Dec. 7, 2010

(54) TOOTHBRUSH WITH SEVERABLE ELECTRICAL CONNECTIONS

(75) Inventors: John Geoffrey Chan, Loveland, OH (US); Aleksey Mikhailovich Pinyayev, West Chester, OH (US); Lowen Robert Morrison, Jr., Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1387 days.

(21) Appl. No.: 10/847,429

(22) Filed: May 17, 2004

(65) Prior Publication Data

US 2005/0050658 A1 Mar. 10, 2005

Related U.S. Application Data

(60) Provisional application No. 60/501,266, filed on Sep. 9, 2003.

(51) Int. Cl.
*A46B 13/02* (2006.01)
*A61C 17/34* (2006.01)

(52) U.S. Cl. .......................... 15/22.1; 15/28
(58) Field of Classification Search .......... 15/22.1, 15/22.2, 28
See application file for complete search history.

(56) References Cited

U.S. PATENT DOCUMENTS

| | | | |
|---|---|---|---|
| 3,261,978 A | 7/1966 | Brenman | |
| 3,309,274 A | 3/1967 | Brilliant | |
| 3,524,088 A | 8/1970 | Ryckman, Jr. | |
| 3,711,700 A | 1/1973 | Westlund et al. | |
| 3,732,416 A | 5/1973 | Audesse et al. | |
| 3,775,800 A | 12/1973 | Veneziani | |
| 4,156,620 A | 5/1979 | Clemens | |
| 4,266,535 A | 5/1981 | Moret | |
| 4,290,433 A | 9/1981 | Alfano | |
| RE31,815 E | 1/1985 | Albano | |
| 4,515,476 A | 5/1985 | Ingmar | |
| 4,590,061 A | 5/1986 | Southard | |
| 4,661,070 A | 4/1987 | Friedman | |
| 4,779,173 A | 10/1988 | Carr et al. | |
| 4,802,851 A * | 2/1989 | Rhoades ..................... 433/93 |
| 4,827,550 A | 5/1989 | Graham et al. | |
| 4,845,795 A | 7/1989 | Crawford et al. | |
| 4,989,287 A | 2/1991 | Scherer | |

(Continued)

FOREIGN PATENT DOCUMENTS

CA 1082408 7/1980

(Continued)

OTHER PUBLICATIONS

U.S. Appl. No. 10/832,168, filed Apr. 26, 2004, Pinyayev, et al.

(Continued)

*Primary Examiner*—Randall Chin

(57) ABSTRACT

Disclosed is an electrical connector having particular application in an oral care implement having a removable and/or replaceable head. In particular, an electric toothbrush having a removable brush head and/or head and neck assembly and a severable electrical connector is disclosed in which the brush head includes one or more elements requiring a source of electrical power. The severable electrical connector provides electrical communication between the brush head and a power source retained within the handle or handle portion of the toothbrush.

9 Claims, 28 Drawing Sheets

U.S. PATENT DOCUMENTS

| | | | |
|---|---|---|---|
| 5,030,090 A | 7/1991 | Maeda et al. | |
| 5,032,178 A | 7/1991 | Cornell | |
| 5,033,150 A | 7/1991 | Gross et al. | |
| 5,033,960 A * | 7/1991 | Heil | 433/29 |
| 5,123,845 A | 6/1992 | Vassiliadis et al. | |
| 5,160,194 A | 11/1992 | Feldman | |
| 5,226,206 A | 7/1993 | Davidovitz et al. | |
| 5,253,382 A | 10/1993 | Beny | |
| 5,275,564 A | 1/1994 | Vassiliadis et al. | |
| 5,306,143 A | 4/1994 | Levy | |
| 5,311,632 A * | 5/1994 | Center | 15/22.1 |
| 5,337,435 A | 8/1994 | Krasner et al. | |
| 5,353,460 A | 10/1994 | Bauman | |
| 5,359,747 A | 11/1994 | Amakasu | |
| 5,429,120 A | 7/1995 | Lewitus | |
| 5,435,724 A | 7/1995 | Goodman et al. | |
| 5,448,792 A | 9/1995 | Wiedemann et al. | |
| 5,504,959 A | 4/1996 | Yukawa et al. | |
| 5,617,601 A | 4/1997 | McDougall | |
| 5,645,428 A | 7/1997 | Yarborough | |
| 5,658,148 A | 8/1997 | Neuberger et al. | |
| 5,766,011 A | 6/1998 | Sibner | |
| 5,785,527 A | 7/1998 | Jensen et al. | |
| 5,800,165 A | 9/1998 | Kirsch et al. | |
| 5,813,855 A | 9/1998 | Crisio | |
| 5,836,030 A | 11/1998 | Hazeu et al. | |
| 5,842,245 A | 12/1998 | Pai | |
| 5,852,875 A * | 12/1998 | Dolah | 30/113.1 |
| 5,876,206 A | 3/1999 | Mauer | |
| 5,879,159 A | 3/1999 | Cipolla | |
| 5,894,620 A | 4/1999 | Polaert et al. | |
| 5,921,251 A | 7/1999 | Joshi | |
| 5,957,687 A | 9/1999 | Brilliant | |
| 6,000,083 A | 12/1999 | Blaustein et al. | |
| 6,056,548 A | 5/2000 | Neuberger et al. | |
| 6,086,363 A | 7/2000 | Moran et al. | |
| 6,094,767 A | 8/2000 | Imura | |
| D432,312 S | 10/2000 | Blaustein et al. | |
| 6,135,774 A | 10/2000 | Hack et al. | |
| 6,139,320 A | 10/2000 | Hahn | |
| D433,814 S | 11/2000 | Blaustein et al. | |
| 6,162,055 A | 12/2000 | Montgomery et al. | |
| 6,178,579 B1 | 1/2001 | Blaustein et al. | |
| 6,189,693 B1 | 2/2001 | Blaustein et al. | |
| 6,202,242 B1 * | 3/2001 | Salmon et al. | 15/22.1 |
| 6,231,338 B1 | 5/2001 | DeJong et al. | |
| 6,231,343 B1 | 5/2001 | Ishibashi et al. | |
| 6,237,178 B1 | 5/2001 | Krammer et al. | |
| 6,251,127 B1 | 6/2001 | Biel | |
| 6,291,568 B1 | 9/2001 | Lussey | |
| 6,311,837 B1 | 11/2001 | Blaustein et al. | |
| 6,314,605 B1 | 11/2001 | Solanki et al. | |
| 6,325,623 B1 | 12/2001 | Melnyk et al. | |
| 6,343,400 B1 | 2/2002 | Massholder et al. | |
| 6,343,933 B1 | 2/2002 | Montgomery et al. | |
| 6,360,395 B2 | 3/2002 | Blaustein et al. | |
| 6,371,294 B1 | 4/2002 | Blaustein et al. | |
| D456,998 S | 5/2002 | Blaustein et al. | |
| D457,728 S | 5/2002 | Blaustein et al. | |
| D458,030 S | 6/2002 | Blaustein et al. | |
| D458,455 S | 6/2002 | Blaustein et al. | |
| D459,584 S | 7/2002 | Blaustein et al. | |
| D459,894 S | 7/2002 | Blaustein et al. | |
| D459,895 S | 7/2002 | Blaustein et al. | |
| 6,416,319 B1 | 7/2002 | Cipolla | |
| 6,417,917 B1 | 7/2002 | Jung et al. | |
| 6,419,483 B1 * | 7/2002 | Adam et al. | 433/29 |
| D461,642 S | 8/2002 | Blaustein et al. | |
| 6,439,888 B1 | 8/2002 | Boutoussov et al. | |
| D465,088 S | 11/2002 | Blaustein et al. | |
| 6,485,300 B1 | 11/2002 | Muller et al. | |
| 6,546,585 B1 | 4/2003 | Blaustein et al. | |
| 6,561,802 B2 | 5/2003 | Alexander | |
| 6,561,808 B2 | 5/2003 | Neuberger | |
| 6,564,940 B2 | 5/2003 | Blaustein et al. | |
| 6,581,233 B1 | 6/2003 | Cheng et al. | |
| D476,486 S | 7/2003 | Wang et al. | |
| 6,597,934 B1 | 7/2003 | DeJong et al. | |
| D483,182 S | 12/2003 | Blaustein et al. | |
| 6,702,576 B2 | 3/2004 | Fischer et al. | |
| 6,752,627 B2 | 6/2004 | Lin | |
| 6,760,945 B2 * | 7/2004 | Ferber et al. | 15/22.2 |
| 6,783,363 B2 | 8/2004 | Eguchi et al. | |
| 6,793,490 B2 * | 9/2004 | Bianchetti et al. | 433/29 |
| 6,836,917 B2 * | 1/2005 | Blaustein et al. | 15/22.1 |
| 6,843,981 B1 | 1/2005 | Ishibashi et al. | |
| 6,893,259 B1 | 5/2005 | Reizenson | |
| 6,902,397 B2 * | 6/2005 | Farrell et al. | 433/29 |
| 6,952,855 B2 * | 10/2005 | Lev et al. | 15/28 |
| 6,954,961 B2 * | 10/2005 | Ferber et al. | 15/22.1 |
| 6,957,907 B2 | 10/2005 | Fischer et al. | |
| 2001/0022277 A1 | 9/2001 | Blaustein et al. | |
| 2002/0020645 A1 | 2/2002 | Blaustein et al. | |
| 2002/0029988 A1 | 3/2002 | Blaustein et al. | |
| 2002/0032941 A1 | 3/2002 | Blaustein et al. | |
| 2002/0078514 A1 | 6/2002 | Blaustein et al. | |
| 2002/0119100 A1 | 8/2002 | Okada et al. | |
| 2002/0162180 A1 | 11/2002 | Blaustein et al. | |
| 2002/0182563 A1 | 12/2002 | Boutoussov et al. | |
| 2003/0022126 A1 | 1/2003 | Buchalla et al. | |
| 2003/0059738 A1 | 3/2003 | Neuberger | |
| 2003/0097122 A1 | 5/2003 | Ganz et al. | |
| 2003/0104340 A1 | 6/2003 | Clemans | |
| 2003/0140435 A1 | 7/2003 | Eliav et al. | |
| 2003/0143510 A1 | 7/2003 | Berube-Lauziere et al. | |
| 2003/0198605 A1 | 10/2003 | Montgomery | |
| 2003/0226223 A1 | 12/2003 | Chan | |
| 2004/0019990 A1 | 2/2004 | Farrell et al. | |
| 2004/0023184 A1 | 2/2004 | De Josselin de Jong et al. | |
| 2004/0047816 A1 | 3/2004 | Yamaguchi et al. | |
| 2004/0106081 A1 | 6/2004 | Karazivan et al. | |
| 2004/0109829 A1 | 6/2004 | Nonami et al. | |
| 2004/0138082 A1 | 7/2004 | Sugihara et al. | |
| 2004/0170578 A1 | 9/2004 | Sugihara | |
| 2004/0171505 A1 | 9/2004 | Nonami et al. | |
| 2004/0180008 A1 | 9/2004 | Yamaguchi et al. | |
| 2004/0191729 A1 | 9/2004 | Altshuler et al. | |
| 2004/0193235 A1 | 9/2004 | Altshuler et al. | |
| 2004/0193236 A1 | 9/2004 | Altshuler et al. | |
| 2004/0199227 A1 | 10/2004 | Altshuler et al. | |
| 2004/0204745 A1 | 10/2004 | Altshuler et al. | |
| 2004/0210276 A1 | 10/2004 | Altshuler et al. | |
| 2005/0048434 A1 | 3/2005 | Cipolla et al. | |
| 2005/0050658 A1 | 3/2005 | Chan et al. | |
| 2005/0050659 A1 | 3/2005 | Chan et al. | |
| 2005/0053895 A1 | 3/2005 | Pinyayev et al. | |
| 2005/0053896 A1 | 3/2005 | Pinyayev et al. | |
| 2005/0053898 A1 | 3/2005 | Ghosh et al. | |
| 2005/0064370 A1 | 3/2005 | Duret | |
| 2005/0064371 A1 | 3/2005 | Soukos et al. | |
| 2005/0066459 A1 | 3/2005 | Pinyayev et al. | |
| 2005/0074723 A1 | 4/2005 | Ostler | |
| 2005/0091769 A1 * | 5/2005 | Jimenez et al. | 15/22.1 |
| 2005/0170316 A1 | 8/2005 | Russell et al. | |
| 2005/0256554 A1 | 11/2005 | Malak | |
| 2005/0265933 A1 | 12/2005 | Montgomery et al. | |
| 2005/0274906 A1 | 12/2005 | Riddell | |
| 2006/0008767 A1 | 1/2006 | Whalen | |
| 2006/0048696 A1 | 3/2006 | Yamazaki et al. | |
| 2006/0110700 A1 | 5/2006 | Cipolla et al. | |

FOREIGN PATENT DOCUMENTS

| | | |
|---|---|---|
| CA | 1191003 | 7/1985 |

| | | | | | | |
|---|---|---|---|---|---|---|
| CA | 96826 | 7/2002 | | EP | 1 415 614 | 5/2004 |
| CN | 2274947 | 2/1998 | | EP | 1 457 200 | 9/2004 |
| DE | 1244709 | 7/1967 | | FR | 1357566 | 4/1964 |
| DE | 3328604 | 3/1986 | | FR | 1357570 | 4/1964 |
| DE | 3630153 | 4/1988 | | FR | 1414679 | 9/1965 |
| DE | 3739009 | 6/1989 | | FR | 2368854 | 5/1978 |
| DE | 8900029 | 6/1990 | | GB | 1240438 | 7/1971 |
| DE | 3734860 | 11/1990 | | GB | 2005999 | 5/1979 |
| DE | 3939859 | 6/1991 | | GB | 1583558 | 1/1981 |
| DE | 202004004628 | 8/1991 | | GB | 2191016 | 12/1987 |
| DE | 9215583 | 3/1994 | | GB | 2196258 | 4/1988 |
| DE | 9215595 | 3/1994 | | GB | 2228402 | 8/1990 |
| DE | 29517758 | 4/1996 | | GB | 2274061 | 7/1994 |
| DE | 29505195 | 9/1996 | | GB | 2089042 | 3/2001 |
| DE | 296 21 445 U1 | 4/1997 | | GB | 2094145 | 3/2001 |
| DE | 29517610 | 4/1997 | | GB | 2097844 | 3/2001 |
| DE | 19541429 | 5/1997 | | GB | 2097845 | 3/2001 |
| DE | 29621445 | 5/1997 | | GB | 3008453 | 5/2003 |
| DE | 19708266 | 9/1998 | | GB | 3004567 | 9/2003 |
| DE | 29900775 | 5/1999 | | GB | 3004568 | 9/2003 |
| DE | 299 08 517 U1 | 12/1999 | | GB | 3014059 | 9/2003 |
| DE | 29908517 | 1/2000 | | GB | 3014060 | 9/2003 |
| DE | 19824786 | 10/2000 | | GB | 3006685 | 10/2003 |
| DE | 19950933 | 4/2001 | | GB | 3006686 | 10/2003 |
| DE | 10008753 | 9/2001 | | GB | 2406503 | 4/2005 |
| DE | 10066004 A1 | 12/2001 | | GB | 2416309 | 1/2006 |
| DE | 19654108 | 2/2002 | | GB | 2416310 | 1/2006 |
| DE | 20214259 | 11/2002 | | GB | 2416311 | 1/2006 |
| DE | 10115426 | 3/2003 | | JP | 63-286147 | 11/1988 |
| DE | 10039198 | 8/2003 | | JP | 2-241406 | 9/1990 |
| DE | 20013827 | 9/2003 | | JP | 2-249505 | 10/1990 |
| DE | 20307294 | 11/2003 | | JP | 2-283311 | 11/1990 |
| DE | 10304221 | 11/2004 | | JP | 3-251207 | 11/1991 |
| DE | 20319405 | 4/2005 | | JP | 5-146314 | 6/1993 |
| DE | 202004001004 | 4/2005 | | JP | 5-269024 | 10/1993 |
| DE | 10347258 | 5/2005 | | JP | 6-121710 | 5/1994 |
| DE | 202005002341 | 7/2005 | | JP | 6-189822 | 7/1994 |
| DE | 202005015767 | 2/2006 | | JP | 6-245819 | 9/1994 |
| DE | 202005018891 | 6/2006 | | JP | 6-245820 | 9/1994 |
| DE | 202005019681 | 6/2006 | | JP | 7-116020 | 5/1995 |
| EP | 0 056 877 | 8/1982 | | JP | 7-116024 | 5/1995 |
| EP | 0 054043 | 11/1985 | | JP | 7-93892 | 10/1995 |
| EP | 0 138 119 | 10/1986 | | JP | 8-000356 | 1/1996 |
| EP | 0 238 778 | 9/1987 | | JP | 8-103331 | 4/1996 |
| EP | 0 278 855 | 10/1989 | | JP | 2540444 | 4/1997 |
| EP | 0 406 454 | 1/1991 | | JP | 2656178 | 5/1997 |
| EP | 0 417 963 | 3/1991 | | JP | 9-140454 | 6/1997 |
| EP | 0 516 872 | 12/1992 | | JP | 2719556 | 11/1997 |
| EP | 0 530 646 | 3/1993 | | JP | 10-165228 | 6/1998 |
| EP | 0 637 976 | 11/1993 | | JP | 2804940 | 7/1998 |
| EP | 0 575 274 | 3/1994 | | JP | 2811246 | 8/1998 |
| EP | 0 593 375 | 4/1994 | | JP | 11-004839 | 1/1999 |
| EP | 0 672 387 | 9/1995 | | JP | 11-155638 | 6/1999 |
| EP | 0 651978 | 10/1995 | | JP | 3005608 | 11/1999 |
| EP | 0 527 163 | 3/1996 | | JP | 3045412 | 3/2000 |
| EP | 0 743 029 | 11/1996 | | JP | 2000-217844 | 8/2000 |
| EP | 0 714 632 | 5/1997 | | JP | 2000-344640 | 12/2000 |
| EP | 0 637 438 | 8/1997 | | JP | 2001-114658 | 4/2001 |
| EP | 0 914 808 | 5/1999 | | JP | 2001-218624 | 8/2001 |
| EP | 0 914 809 | 5/1999 | | JP | 2001-299454 | 10/2001 |
| EP | 0 927 544 | 7/1999 | | JP | 2001-299454 A | 4/2002 |
| EP | 1 083 806 | 12/1999 | | JP | 2002-097125 | 4/2002 |
| EP | 1 025 776 | 8/2000 | | JP | 1149976 | 6/2002 |
| EP | 1 048 291 | 11/2000 | | JP | 2002-200101 | 7/2002 |
| EP | 1 101 436 | 5/2001 | | JP | 2002-306515 | 10/2002 |
| EP | 1 118 311 | 7/2001 | | JP | 2002-363051 | 12/2002 |
| EP | 1 138 275 | 10/2001 | | JP | 2003-164334 | 6/2003 |
| EP | 1 151 728 | 11/2001 | | JP | 2003-221321 | 8/2003 |
| EP | 1 174 055 | 1/2002 | | JP | 2003-221322 | 8/2003 |
| EP | 0 973 460 | 2/2002 | | JP | 2003-320243 | 11/2003 |
| EP | 1 192 933 | 4/2002 | | JP | 2004-018444 | 1/2004 |
| EP | 1 393 711 | 3/2004 | | JP | 2004-105705 | 4/2004 |
| EP | 1 407 723 | 4/2004 | | JP | 2004-154211 | 6/2004 |

| | | | | | | |
|---|---|---|---|---|---|---|
| JP | 2004-242841 | 9/2004 | | WO | WO 01/72301 A1 | 10/2001 |
| JP | 2004-323417 | 11/2004 | | WO | WO 01/76595 A1 | 10/2001 |
| JP | 2005-046388 | 2/2005 | | WO | WO 02/05812 A1 | 1/2002 |
| JP | 2005-058594 | 3/2005 | | WO | WO 98/27891 | 2/2002 |
| JP | 2005-081126 | 3/2005 | | WO | WO 02/021970 A1 | 3/2002 |
| JP | 2005-343813 | 12/2005 | | WO | WO 02/22097 A1 | 3/2002 |
| JP | 2006-061292 | 3/2006 | | WO | WO 96/36396 | 3/2002 |
| KR | 1997-0000408 | 1/1997 | | WO | WO 02/061683 A3 | 8/2002 |
| KR | 1997-0000409 | 1/1997 | | WO | WO 02/088290 A1 | 11/2002 |
| KR | 125188 | 10/1997 | | WO | WO 02/096896 A1 | 12/2002 |
| RU | 2 122 819 C1 | 12/1998 | | WO | WO 03/007756 A1 | 1/2003 |
| TW | 26360 | 3/1978 | | WO | WO 03/013380 A1 | 2/2003 |
| TW | 212909 | 9/1993 | | WO | WO 03/013653 A1 | 2/2003 |
| WO | WO 89/06942 A1 | 8/1989 | | WO | WO 03/026528 A1 | 4/2003 |
| WO | WO 91/06258 A1 | 5/1991 | | WO | WO 03/029140 A1 | 4/2003 |
| WO | WO 91/13570 | 9/1991 | | WO | WO 03/039396 A1 | 5/2003 |
| WO | WO 92/06671 A1 | 4/1992 | | WO | WO 03/047454 A1 | 6/2003 |
| WO | WO 92/13499 A1 | 8/1992 | | WO | WO 03/047477 A1 | 6/2003 |
| WO | WO 92/19178 | 11/1992 | | WO | WO 03/059305 A1 | 7/2003 |
| WO | WO 90/11728 | 4/1993 | | WO | WO 03/076015 A1 | 9/2003 |
| WO | WO 93/15688 A1 | 8/1993 | | WO | WO 03/077996 A2 | 9/2003 |
| WO | WO 93/18715 A1 | 9/1993 | | WO | WO 03/082049 A | 10/2003 |
| WO | WO 93/21991 A1 | 11/1993 | | WO | WO 03/082050 A1 | 10/2003 |
| WO | WO 94/09718 A1 | 5/1994 | | WO | WO 03/089063 A1 | 10/2003 |
| WO | WO 94/09850 A1 | 5/1994 | | WO | WO 03/103531 A1 | 12/2003 |
| WO | WO 94/22386 A1 | 10/1994 | | WO | WO 2004/006065 A2 | 1/2004 |
| WO | WO 95/07731 A1 | 3/1995 | | WO | WO 2004/012593 A1 | 2/2004 |
| WO | WO 95/10243 A1 | 4/1995 | | WO | WO 2004/012621 A1 | 2/2004 |
| WO | WO 95/26692 A1 | 10/1995 | | WO | WO 2004/014181 A1 | 2/2004 |
| WO | WO 96/03089 A1 | 2/1996 | | WO | WO 2004/014182 A1 | 2/2004 |
| WO | WO 96/09019 | 3/1996 | | WO | WO 2004/024080 A2 | 3/2004 |
| WO | WO 96/10373 | 4/1996 | | WO | WO 2004/026075 A1 | 4/2004 |
| WO | WO 96/38100 | 12/1996 | | WO | WO 2004/026162 A2 | 4/2004 |
| WO | WO 97/16152 A1 | 5/1997 | | WO | WO 2004/028235 A2 | 4/2004 |
| WO | WO 97/21420 A1 | 6/1997 | | WO | WO 2004/030891 A1 | 4/2004 |
| WO | WO 98/06456 A1 | 2/1998 | | WO | WO 2004/033040 A1 | 4/2004 |
| WO | WO 98/18398 A1 | 5/1998 | | WO | WO 2004/043204 A2 | 5/2004 |
| WO | WO 98/18399 A1 | 5/1998 | | WO | WO 02/060401 A1 | 6/2004 |
| WO | WO 98/23219 A1 | 6/1998 | | WO | WO 2004/045538 A2 | 6/2004 |
| WO | WO 98/30169 A1 | 7/1998 | | WO | WO 2004/049966 A2 | 6/2004 |
| WO | WO 98/30494 A1 | 7/1998 | | WO | WO 2004/052230 A1 | 6/2004 |
| WO | WO 98/32396 A1 | 7/1998 | | WO | WO 2004/052407 A1 | 6/2004 |
| WO | WO 98/58595 A1 | 12/1998 | | WO | WO 02/068576 A1 | 7/2004 |
| WO | WO 99/07253 A1 | 2/1999 | | WO | WO 2004/069084 A1 | 8/2004 |
| WO | WO 99/07305 A1 | 2/1999 | | WO | WO 02/087514 A1 | 9/2004 |
| WO | WO 99/10046 A1 | 3/1999 | | WO | WO 2004/082499 A1 | 9/2004 |
| WO | WO 99/10828 A1 | 3/1999 | | WO | WO 2004/084752 A2 | 10/2004 |
| WO | WO 99/12448 A1 | 3/1999 | | WO | WO 2004/087252 A2 | 10/2004 |
| WO | WO 97/01298 | 4/1999 | | WO | WO 2004/096074 A2 | 11/2004 |
| WO | WO 99/15099 A1 | 4/1999 | | WO | WO 2004/103171 A2 | 12/2004 |
| WO | WO 99/37236 A1 | 7/1999 | | WO | WO 2004/103471 A1 | 12/2004 |
| WO | WO 99/43387 A1 | 9/1999 | | WO | WO 2004/104927 A2 | 12/2004 |
| WO | WO 99/52596 A1 | 10/1999 | | WO | WO 2004/105874 A1 | 12/2004 |
| WO | WO 99/56810 A1 | 11/1999 | | WO | WO 2004/108003 A1 | 12/2004 |
| WO | WO 99/59462 A1 | 11/1999 | | WO | WO 2004/108004 A1 | 12/2004 |
| WO | WO 99/63859 A1 | 12/1999 | | WO | WO 2004/112535 A1 | 12/2004 |
| WO | WO 99/63900 A1 | 12/1999 | | WO | WO 2004/112538 A1 | 12/2004 |
| WO | WO 00/07044 A1 | 2/2000 | | WO | WO 2004/112637 A2 | 12/2004 |
| WO | WO 00/07482 A1 | 2/2000 | | WO | WO 2005/002458 A2 | 1/2005 |
| WO | WO 00/07514 A1 | 2/2000 | | WO | WO 2005/004745 A1 | 1/2005 |
| WO | WO 00/07515 A1 | 2/2000 | | WO | WO 02/067802 A1 | 2/2005 |
| WO | WO 98/10711 | 2/2000 | | WO | WO 2005/009270 A1 | 2/2005 |
| WO | WO 00/25665 A1 | 5/2000 | | WO | WO 2005/018475 A2 | 3/2005 |
| WO | WO 00/37927 A1 | 6/2000 | | WO | WO 2005/023130 A2 | 3/2005 |
| WO | WO 00/62701 A2 | 10/2000 | | WO | WO 2005/023131 A2 | 3/2005 |
| WO | WO 95/22938 | 10/2000 | | WO | WO 2005/023143 A2 | 3/2005 |
| WO | WO 01/10327 A1 | 2/2001 | | WO | WO 2005/023144 A2 | 3/2005 |
| WO | WO 01/12181 A1 | 2/2001 | | WO | WO 2005/023145 A2 | 3/2005 |
| WO | WO 01/26572 A1 | 4/2001 | | WO | WO 2005/023146 A2 | 3/2005 |
| WO | WO 01/26576 A1 | 4/2001 | | WO | WO 2005/025670 A1 | 3/2005 |
| WO | WO 01/51005 A2 | 7/2001 | | WO | WO 2005/041713 A1 | 5/2005 |
| WO | WO 01/62289 A2 | 8/2001 | | WO | WO 2005/046793 A2 | 5/2005 |
| WO | WO 01/66030 A1 | 9/2001 | | WO | WO 2005/065572 A1 | 7/2005 |

| | | | |
|---|---|---|---|
| WO | WO 2005/067764 A1 | 7/2005 |
| WO | WO 03/103529 A1 | 8/2005 |
| WO | WO 2005/070129 A2 | 8/2005 |
| WO | WO 2005/072642 A1 | 8/2005 |
| WO | WO 2005/087171 A1 | 9/2005 |
| WO | WO 2005/094719 A1 | 10/2005 |
| WO | WO 2005/099757 A1 | 10/2005 |
| WO | WO 2005/107638 A1 | 11/2005 |
| WO | WO 2005/099513 A1 | 12/2005 |
| WO | WO 2005/120382 A1 | 12/2005 |
| WO | WO 2005/122948 A1 | 12/2005 |
| WO | WO 2005/123023 A1 | 12/2005 |
| WO | WO 2006/003598 A1 | 1/2006 |
| WO | WO 2006/006808 A1 | 1/2006 |
| WO | WO 2006/007136 A2 | 1/2006 |
| WO | WO 2006/012752 A1 | 2/2006 |
| WO | WO 2006/014309 A2 | 2/2006 |
| WO | WO 2006/014363 A2 | 2/2006 |
| WO | WO 2006/014364 A2 | 2/2006 |
| WO | WO 2006/014368 A2 | 2/2006 |
| WO | WO 2006/014369 A2 | 2/2006 |
| WO | WO 2006/014370 A2 | 2/2006 |
| WO | WO 2006/014371 A2 | 2/2006 |
| WO | WO 2006/014402 A2 | 2/2006 |
| WO | WO 2006/014897 A2 | 2/2006 |
| WO | WO 2006/015196 A2 | 2/2006 |
| WO | WO 2006/020698 A1 | 2/2006 |
| WO | WO 2006/026129 A1 | 3/2006 |
| WO | WO 2006/028099 A1 | 3/2006 |
| WO | WO 2006/031242 A1 | 3/2006 |
| WO | WO 2006/034133 A1 | 3/2006 |
| WO | WO 2006/034281 A1 | 3/2006 |
| WO | WO 02/071970 | 4/2006 |
| WO | WO 93/09847 | 4/2006 |
| WO | WO 2006/035443 A2 | 4/2006 |
| WO | WO 2006/035444 A2 | 4/2006 |
| WO | WO 2006/044099 A1 | 4/2006 |
| WO | WO 2006/047868 A1 | 5/2006 |
| WO | WO 2006/050452 A2 | 5/2006 |
| WO | WO 2006/051619 A1 | 5/2006 |
| WO | WO 2006/053207 A2 | 5/2006 |
| WO | WO 2006/055369 A1 | 5/2006 |
| WO | WO 2006/055571 A2 | 5/2006 |
| WO | WO 2006/055572 A1 | 5/2006 |
| WO | WO 2006/055574 A2 | 5/2006 |
| WO | WO 2006/060547 A2 | 6/2006 |
| WO | WO 2006/063131 A2 | 6/2006 |
| WO | WO 2006/063202 A2 | 6/2006 |
| WO | WO 2006/063318 A1 | 6/2006 |
| WO | WO 2006/014365 A2 | 9/2006 |

OTHER PUBLICATIONS

U.S. Appl. No. 10/842,302, filed May 10, 2004, Pinyayev, et al.
U.S. Appl. No. 10/887,644, filed Jul. 9, 2004, Pinyayev, et al.
U.S. Appl. No. 10/887,667, filed Jul. 9, 2004, Ghosh, et al.
U.S. Appl. No. 10/888,206, filed Jul. 9 2004, Chan, et al.
American Opto Plus LED Corp, Part No. L513UBC-S (spec sheet) Jul. 10, 2001.
American Opto Plus LED Corp, Part No. L513NBC-15D (spec sheet) Nov. 10, 2002.
American Opto Plus LED Corp, Part No. L314WC-15DS (spec sheet) Jul. 10, 2001.
American Opto Plus LED Corp, Part No. L513LBC-15D (spec sheet) May 21, 2001.
Roithner Lasertechnik, Part No. 5W4HCA-H, (spec sheet) Mar. 8, 2004.
SunLED, XLBB12WH (spec sheet), Sep. 11, 2003.
Marktech Optoelectronics, LC503QBL1-15G (spec sheet) Nov. 5, 2003.
Marktech Optoelectronics, LC503QBL1-15H (spec sheet) Nov. 5, 2003.
Super Bright LEDs, Inc. (spec sheet) Jan. 2002.
Super Bright LEDs, Inc. RL5-B4630 (spec sheet) Jan. 2002.
Super Bright LEDs, Inc. RL5-B3025 (spec sheet) Jan. 2002.
Super Bright LEDs, Inc. RL5-B5515 (spec sheet) Jan. 2002.
Lumileds Lighting Luxeon Emitter Data Sheet Sep. 20, 2004.
OPTO DIODE CORP, OD-470 (spec sheet) Apr. 2002.
OPTO DIODE CORP, OD-470L (spec sheet) Apr. 2002.
Roithner Lasertechnik, M3L1 Series spec sheet May 14, 2003.
Roithner Lasertechnik, EP2012-150B1 Series spec sheet, Oct. 23, 2003.
Nichia, Model NSCx190D spec sheet, Apr. 1, 2002.
International Search Report with Written Opinion dated Feb. 28, 2005.

\* cited by examiner

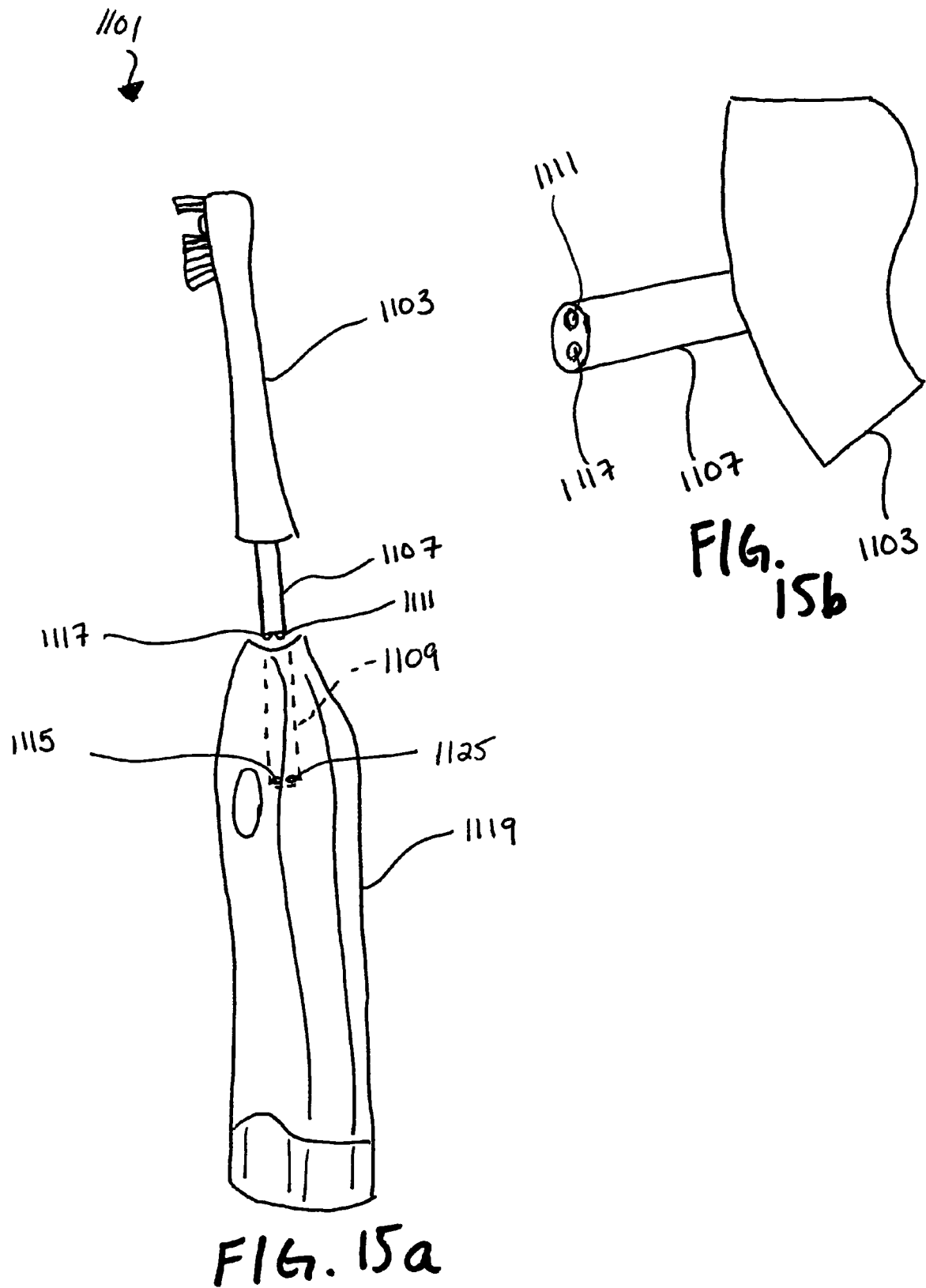

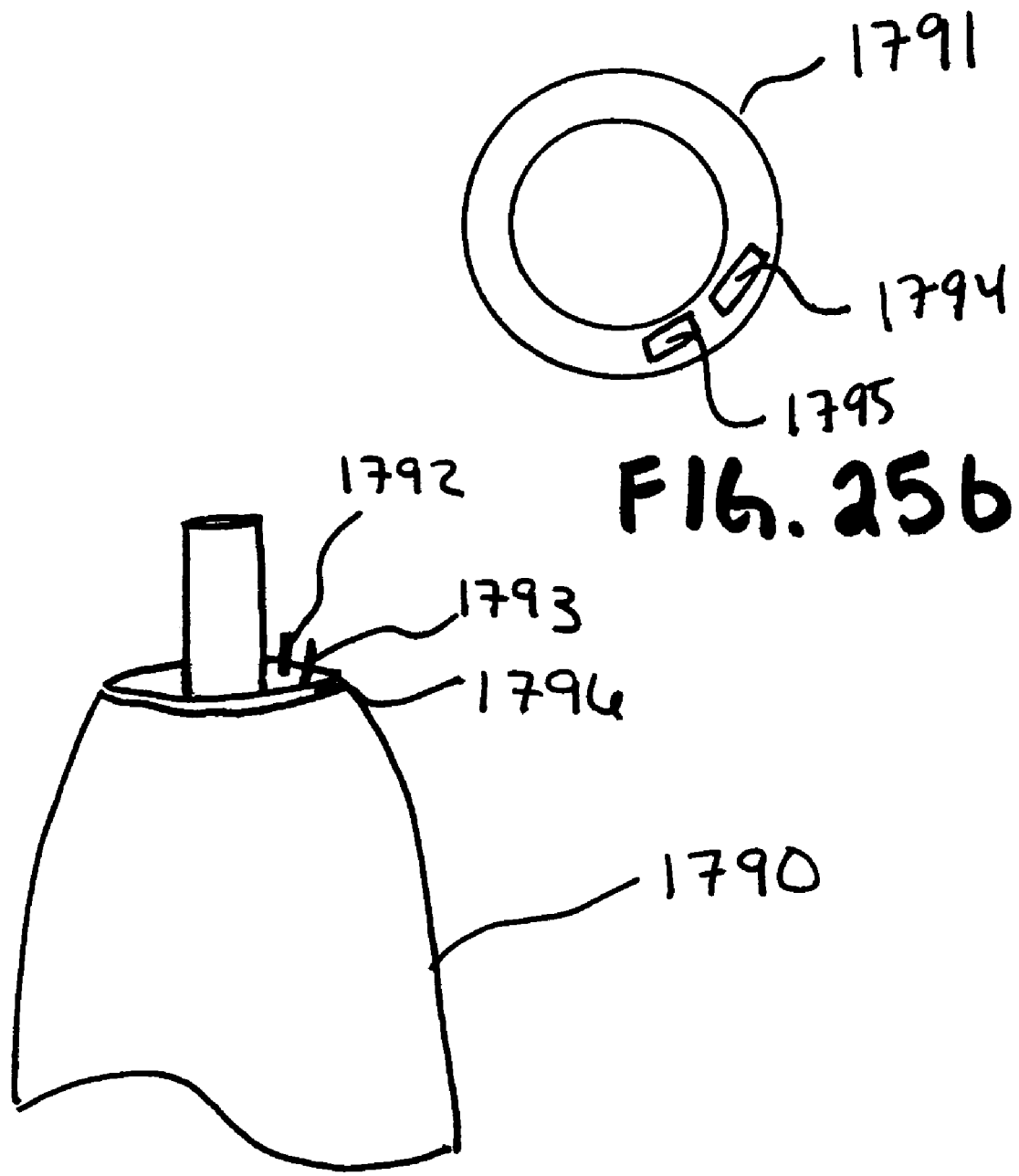

TOOTHBRUSH WITH SEVERABLE ELECTRICAL CONNECTIONS

CROSS REFERENCE TO RELATED APPLICATION

This application claims the benefit of U.S. provisional application Ser. No. 60/501,266 filed Sep. 9, 2003 which is herein incorporated by reference.

FIELD OF THE INVENTION

The present invention relates to electric toothbrushes having a separable brush head that utilize one or more elements on the brush head that require a source of electrical power. More particularly, the present invention relates to a battery powered toothbrush utilizing selectively engageable electrical connectors between the head and handle of the toothbrush.

BACKGROUND OF THE INVENTION

Electric toothbrushes are known that utilize a replaceable or interchangeable brush head which is releasably engageable with a handle or body portion. For example, U.S. Pat. No. 5,404,608 to Hommann discloses an electric toothbrush having a handle with a push-on brush component. U.S. Pat. No. 4,880,382 to Moret et al. and U.S. Pat. No. 5,435,034 to Bigler et al. disclose electric toothbrushes having brush heads that are replaceable and removable from a handle or body portion of the brush. Both the '382 patent and the '034 patent utilize a slotted engagement mechanism between the brush head and the handle portion of the brush. U.S. Pat. No. 5,465,444 to Bigler et al. describes an electric toothbrush having a brush head that is said to "slip-on" a handle portion.

However, a need exists for an electric toothbrush having a removable brush head with an electrically powered element. Specifically, a need exists for a removable brush head which may be securely and easily engaged or disengaged with a handle or body portion of the toothbrush, in conjunction with a selectively engageable electrical connection between the head and the handle.

SUMMARY OF THE INVENTION

The present invention provides an oral care implement for use in the mouth comprising a handle defining a hollow interior region, and a head that is removable from and attachable to the handle. The head includes at least one electrically powered element. The oral care implement also comprises at least one electrical connector; wherein the electrical connector provides electrical communication between the head and the handle upon attachment of the head to the handle.

BRIEF DESCRIPTION OF THE DRAWINGS

The invention may take physical form in certain parts and arrangements of parts, the embodiments of which will be described in detail in this specification and illustrated in the accompanying drawings which form a part hereof, and wherein:

FIG. 15a is a partial view illustrating attachment of a head to a handle of a toothbrush in accordance with the present invention.

FIG. 15b is a partial exploded view illustrating the engagement member extending from the head portion of a toothbrush in accordance with the present invention.

FIGS. 25a and 25b are partial views of the head and the neck depicting another embodiment of the present invention.

DETAILED DESCRIPTION OF THE EMBODIMENTS

Figure 1:
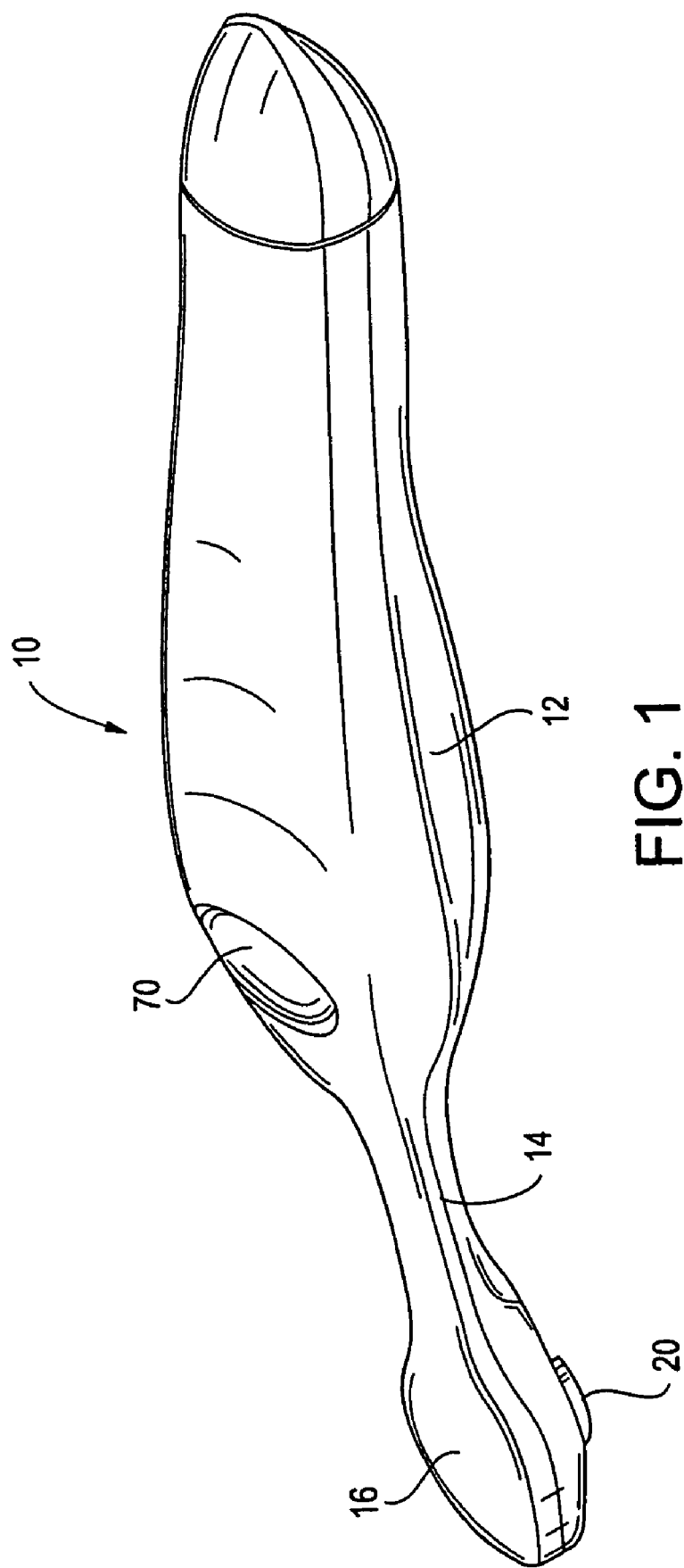
FIG. 1 is a perspective view of an electric toothbrush having a removable brush head in accordance with the present invention.

All printed publications, patents, and patent applications referenced herein are incorporated herein by reference. Generally, the present invention relates to an oral care implement for use in the mouth having a replaceable or removable head and/or neck and one or more electrical elements on the brush head, including, but not limited to, light-emitting elements. Such oral care implements can include, but are not limited to, electric toothbrushes, powered flossers, tooth polishers, gum massagers etc. For simplicity sake hereinafter the present invention will be discussed as embodied in an electric toothbrush. Such electric toothbrushes can be used in personal hygiene to clean one's teeth and gums using a motorized movement, while the electrical element is activated, such as a light-emitting element which can illuminate the region of brushing, including the teeth and/or gums. The present invention includes any type of electrically powered elements used or provided on the head. Furthermore, the present invention relates to the use and incorporation of selectively engageable electrical connectors in an electric toothbrush having a removable brush head and that provides electrical communication between the head of the toothbrush and the handle of the toothbrush. The head of the toothbrush can further comprise a neck, to which the handle of the toothbrush can be attached. Further, the handle of the toothbrush can comprise a neck, to which the head of the toothbrush can be attached. For simplicity hereinafter the connections discussed will be between the head and the handle of the toothbrush. However, it should be appreciated that this discussion also includes connections between the head and the neck, and/or a head and neck assembly connecting to the handle and/or the body. All of these connections have the similar elements, but a different location of the connection along the length of the toothbrush.

In one embodiment, an illuminated electric toothbrush is provided that includes an elongated handle, a head, and a neck extending from the head to form a head and neck assembly. This head and neck assembly can be attached to the handle. The present invention includes embodiments in which the head and neck as a single integral assembly, are removable from the handle of the toothbrush. However, it is contemplated that the neck and handle can also be an assembly, from which a head is removable. Provided along the mating or engagement regions of the removable portions is the severable electrical connector described herein. One or more electrical elements such as light-emitting elements can be disposed on the head, adjacent to, on, or in one or more static or moving bristle holders or any combination thereof. The bristle holders may have bristles disposed thereon, and the bristles may be formed into one or groups of tufts. These aspects are described in greater detail herein.

The toothbrushes further comprise an electrical connector. An electrical connector is a system of components on the head, neck and/or handle of an electric toothbrush that when connected provides an electrical path and electrical communication between the head and the handle. As the head is removable from the handle portion of the toothbrush, the electrical connector can be designed such that the electrical connection can be severed or disengaged upon removal of the head and can be readily reconnected upon reattachment. An electrical connector comprises at least one electrical input and at least one electrical output. The electrical connector can include, but is not limited to, components which come into mechanical contact with each other "contacts", inductive components which electrically connect the head to the handle via a magnetic field, and capacitive components which electrically connect the head to the handle with an electric field created when a capacitor is formed. Provided along the region of engagement between the handle or body and the head is an electrical connector, examples of which are described herein. The toothbrush can also have more than one connector. It is also contemplated that if a neck extends from either the head and/or the handle, a portion of the connector can be disposed on the neck.

Providing a readily separable engagement configuration between a brush head, and a handle in an electric toothbrush offers several advantages. First, the brush head or handle for that matter may be easily replaced. The brush head may be easily interchanged with another brush head depending upon the particular preferences of a consumer. Furthermore, such quick and simple engagement provides ease of assembly, and also promotes storage and shipping concerns in that the relatively long length of the brush may be significantly reduced In certain embodiments, a toothbrush having a removable head utilizes a member projecting outward from one of the handle or head portions of the toothbrush that is received by a corresponding recess, slot, or receiving region defined in the other portion of the toothbrush. The member and receiving region cooperate with one another to provide selective removal of the head from the handle, and reattachment of the head to the handle. In such a configuration, an electrical connector is positioned proximate to the member and its receiving region. For example, if the connector includes two electrically conducting contacts, a first contact can be disposed on the member and the second contact can be disposed within the receiving region. The contacts are positioned such that upon attachment of the head to the handle and thus, engagement of the head within the receiving region, the contacts are positioned in electrical communication with each other thereby providing an electrical pathway between the handle and the head of the toothbrush.

In an alternate embodiment, the engagement assembly between the housing and brush head may utilize a screw or threaded configuration in which one of the housing and brush head includes a radially projecting screw member, and the other defines a groove or recessed region that is configured to receive the projecting screw member. A corresponding electrical connector is provided, for example electrical contacts can be disposed on the mating surfaces of the engagement assembly.

Other engagement configurations can be used for providing a toothbrush having a removable head and handle. For example, the present invention includes, but is not limited to engagement configurations utilizing a male-female arrangement, a releasable locking pin arrangement, a releasable detent arrangement, a snap-fit arrangement, a friction fit arrangement, and combinations of these configurations. The severable electrical connector can be provided between the head and handle portion, and have components of the connector adjacent or within the regions of engagement or mating between the head and handle portion. However, it is contemplated that the head components of the connector can be received within the handle portion of the toothbrush and/or the handle components of the toothbrush can be received within the head portion of the toothbrush.

In any or all of the embodiments herein, one or more connector wiping elements can be provided that serve to wipe the electrical connector face of one or more of the connectors as the head is re-attached to the handle of the toothbrush. Such a wiping element is provided and positioned such that upon engagement of the head and handle, the wiping element passes over and essentially wipes the outer face of the electrical connector. This action serves to clean the connector face and remove any water or debris accumulated thereon. The wiping element can be formed from nearly any element, such as, but not limited to, a pliable rubber or other elastomeric material.

The brush head of the toothbrushes defines a longitudinal axis, and includes one or more moving bristle holders and, optionally, one or more static or fixed bristle holders. The moving bristle holders may rotate, swivel, gyrate, oscillate, linearly reciprocate, or undergo any combination of motions. The type of motion provided by the electric toothbrushes of the present invention can be widely varied. The static bristle holders and the arrangement of the static bristles disposed thereon can also be widely varied. Examples of some bristle holder motions and bristle arrangements suitable for use with the present invention are described in US 20030126699; US 20030084525; US 20030084524; US 20030084526; and WO 03/063723; and WO 03/063722. The bristles can be made from conventional non-elastomeric materials, such as polyethylene, or can be made from elastomeric materials such as natural or synthetic rubbers, polyolefins, polyetheramides, polyesters, styrenic polymers, polyurethanes, etc., or a combination of materials.

The handle of the toothbrushes has a hollow portion with a motor disposed therein that is operably connected to the moving bristle holders. A shaft extends from the motor through the neck and into at least a portion of the head. The shaft may rotate, oscillate, linearly reciprocate, gyrate, or orbit when driven by the motor in order to impart one or more motions to the moving bristle holders. A gearing arrangement can be provided between the motor and the shaft or between the shaft and the moving bristle holders in order to impart motion thereto. Exemplary shaft and/or gearing arrangements are shown in U.S. Pat. Nos. 6,360,395; 5,617,601; 6,178,579; 6,189,693; 6,360,395; and 6,371,294 as well as in other patents and patent publications referenced herein. The handle also has a power source, such as one or more batteries, disposed therein for powering the motor and the electrical elements disposed on the brush head, such as for example light-emitting elements. Alternatively, the electric toothbrush may be connected to an external power source for powering the motor. A switch is disposed on the handle for activating the motor and/or light-emitting elements. The switch includes an actuator button and a metal contact. The switch is manually depressed by pressing a molded actuator button down, which presses against a metal contact, completing the circuit, as in a conventional momentary switch. The switch can also activate one or more light-emitting elements or other electrical element disposed on the head of the toothbrush.

In accordance with the present invention, some type of releasable engagement is utilized between the drive shaft and one or more movable bristle carriers disposed or otherwise retained along the brush head. For example, a "snap-fit" engagement assembly could be utilized between an end of a drive shaft extending within the brush head, and a movable bristle carrier disposed on the brush head. It will be appreciated that a releasable engagement assembly be utilized at some location or point in the drive mechanism so that the brush head and handle can be readily separated from one another.

In certain embodiments of the toothbrush wherein the components of the connector includes contacts, the contacts can engage one another directly, in a face-to-face fashion as the head is engaged with the handle of the toothbrush. In certain embodiments, the faces of the respective contacts slide across each other, or at least partially so, during the engagement process. The various contacts may be in the form of relatively flat surfaces that contact each other to provide electrical communication. Or, the contacts may utilize a male-female connection as known in the art, including a pin-socket or plug-receiver configuration. The contacts may also utilize sloping or ramp surfaces that contact each other, or depending upon the particular application, may engage each other with relatively large contacting forces due to the ramped configuration. Alternately, or in addition, the contacts may include one or more spring members or other biasing members that impart a force to one or both contacts to further promote the establishment of electrical communication between the contacts. However, the connectors may use the aforementioned designs to come into electrical communication, thereby providing electrical power to the electrical element disposed on the head of the toothbrush, without having mechanical connection i.e. electrical communication established by induction or capacitance. Regardless of the type of connector, once the head and handle are engaged with one another, the connectors are in a configuration and position to provide electrical communication is provided between the head and the handle.

A wide array of connector designs, shapes, and configurations may be utilized in the toothbrushes according to the present invention. In one aspect, a sliding rail configuration is used in which one or more rails are provided on either the brush head or handle, and a receiving slot or recessed region is defined in the other, e.g. brush head or handle, that is of a size and orientation to receive the rails when the brush head and handle are engaged with each other. Contacts can be incorporated in these one or more rail(s) and slot(s) to provide electrical communication between the brush head and handle when the head engages the handle. Specifically, one or more pairs of the contacts are incorporated directly on the exposed surfaces of the rail(s) and slot(s). The respective contacts can be aligned and positioned such that upon final engagement between the brush head and the handle, the contacts provide electrical communication between the brush head and the handle.

In another embodiment, one or more contacts are positioned on side posts or otherwise outwardly projecting members of a brush head or handle that, upon engagement with a corresponding structure provided on the other head or handle, are in electrical communication with one or more additional contacts. Additionally, the handle and/or head, and/or portions of the handle and/or head can comprise electrically conductive substrates such that the handle and/or the head, or portions thereof, can be the electrically conductive contacts. Regardless of the contact placement, the resulting electrical communication enables electrical power to be transferred from the handle region to the brush head of the toothbrush.

In yet another embodiment, electrical communication is established by an axial configuration in which the respective contacts are brought into electrical communication with one another by rotating one of the brush head or handle portion with respect to the other. This configuration may be achieved with a variety of arrangements of electrical contacts. For example, circular, semi-circular, or arcuate shaped contacts may be used. The contacts may be appropriately positioned on engaging regions of the brush head and the handle.

In yet another embodiment electrical communication is established between the head and the handle by induction. In this embodiment the head has a secondary coil which is connected to the electrical element disposed on the head of the toothbrush, and the handle has a primary coil which is connected to the battery. When the head and handle are connected, the primary coil and secondary coil are magnetically coupled to transfer electricity. Further electrical communication can be established between the head and the handle with capacitance by including the appropriate conductive materials in the handle, which are further connected to the battery, and the head, which are further connected to the electrical element disposed on the head. When the head is connected to the handle the two pieces of conductor are separated by a distance such that the two pieces of conductor form a capacitor.

Material selection for the components of the connector is also another important aspect of the present invention. Generally, a wide variety of metals and non-metallic materials may be used for the components of connectors. Suitable metals include, but are not limited to copper, platinum, silver, nickel, aluminum, gold, tungsten, and alloys of these metals.

Electrically conductive non-metallic materials can be used such as electrically conductive polymers. The term "electrically conductive non-metallic materials" as used herein includes materials comprising one or more non-metals and one or more metals, such as polymeric compositions containing metal particles. Often such compounds are made by mixing solid conductive particles such as carbon black, stainless steel fibers, silver or aluminum flakes or nickel-coated fibers with electrically insulating bulk thermoplastics, for example polystyrene, polyolefins, nylons, polycarbonate, acrylonitrile-butadiene-styrene co-polymers (ABS), and the like.

Recently, there has been an increased interest in replacing carbon black or metal particle-filled compounds of the above-described type with intrinsically electrically conductive polymers and their blends with common insulating polymers including, but not limited to polyanilines. Polyaniline (or abbreviated PANI) and its synthesis and the preparation of the electrically conductive form of this polymer by, for example, contacting polyanilines with protonic acids resulting in salt complexes has been described in the prior art. Additionally, electrically conductive polymers are known and used in industrial settings, particularly in the manufacture of electronic component parts. Some examples of electrically conductive polymer compositions are illustrated in U.S. Pat. Nos. 5,256,335; 5,281,363; 5,378,403; 5,662,833; 5,958,303; 6,030,550; and 6,149,840. Particularly attractive electrically conductive polymer compositions for use in the connector assemblies described herein include those polymers described in U.S. Pat. Nos. 5,866,043 and 6,685,854. The term "electrically conductive non-metallic materials" as used herein also includes these types of compositions.

Another electrically conductive substrate suitable for use in the present invention is discussed in U.S. Pat. Nos. 6,291,568, 6,495,069, and 6,646,540. This substrate has a first level of conductance when quiescent, or inactive, and a second level of conductance resulting from a change of stress; i.e. mechanical or electrical stress. The mechanical stress can include stretching and/or compressing. This substrate comprises a granular composition, each granule of which comprises at least one substantially non-conductive polymer and at least one electrically conductive filler. The conductive filler can be one or more metals, other conductive or semi-conductive elements and oxides or intrinsically conductive semiconductive inorganic or organic polymers. The granules are typically up to 1 mm, and the granule (conductor) to polymer volumetric ratio is suitably at least 3:1. It is contemplated that other substrates which conduct electricity when compressed are suitable for use in the present invention.

As previously noted, the toothbrushes can employ one or more electrically powered elements incorporated or otherwise included in the brush head that utilize a source of electrical power. In the toothbrushes described herein, an electrical power source, e.g. one or more batteries, is retained within the handle position of the toothbrush. The electrical connectors described herein establish and provide electrical communications between the brush head and the electrically powered elements requiring electrical power disposed thereon, and the power source, typically residing in the handle of the toothbrush.

Referring now to the drawings wherein the showings are for the purposes of illustrating aspects of the invention only and not for purposes of limiting same, FIGS. 1-4, and specifically, FIG. 1 shows an illuminated electric toothbrush 10 according to an embodiment of the present invention. As shown in FIG. 1, the electric toothbrush includes a handle 12 and a neck 14 attached to the handle 12. A head 16 is attached to neck 14. Typically, the head is larger than the neck 14, which is also typically smaller than the handle 12. The neck and handle are releasably connected and contain corresponding structures for their physical engagement and for establishing electrical communication between the light-emitting element and the power source. The handle 12 of the toothbrush may include one or more areas to facilitate gripping of the toothbrush such as regions 70 and 72.

Figure 2:
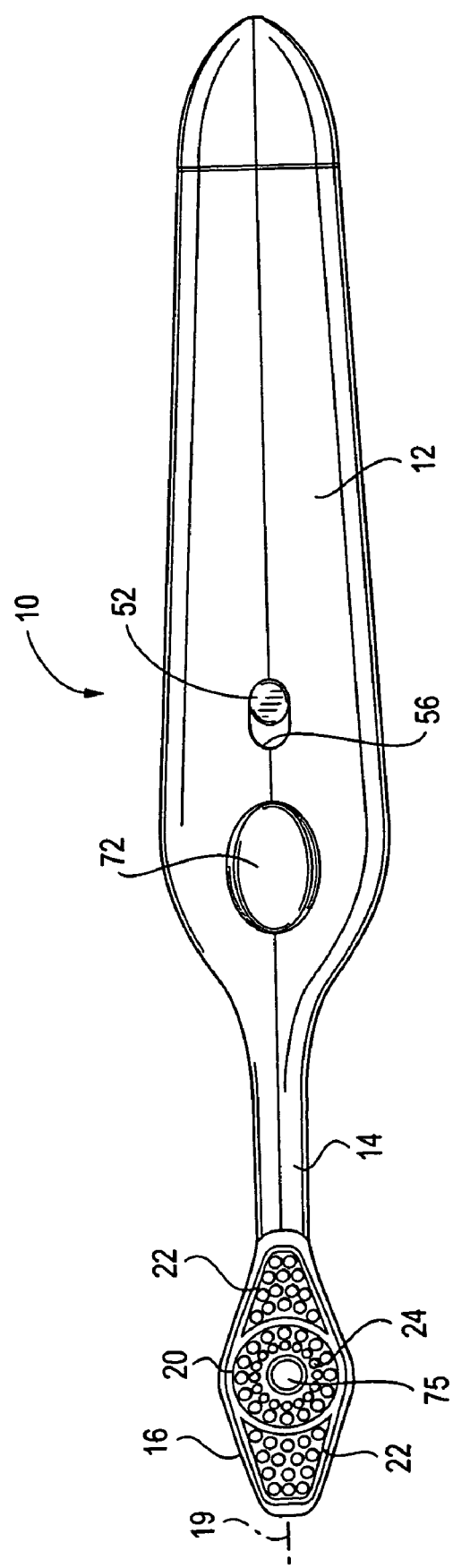
FIG. 2 is a top planar view of the electric toothbrush of FIG. 1.

Referring now to FIG. 2, the head 16 defines a longitudinal axis 19, and includes a moving bristle holder 20 and static bristle holders 22. The static bristle holders 22 are located on opposite sides of the moving bristle holder 20. The moving bristle holder 20 is located at the center of the head 16. The moving bristle holder 20 supports and includes a plurality of moving bristles 24 disposed thereon. The moving bristle holder oscillates about an axis approximately normal to the longitudinal axis 19 of the head 16, although other motions may be provided as previously described.

Figure 3:
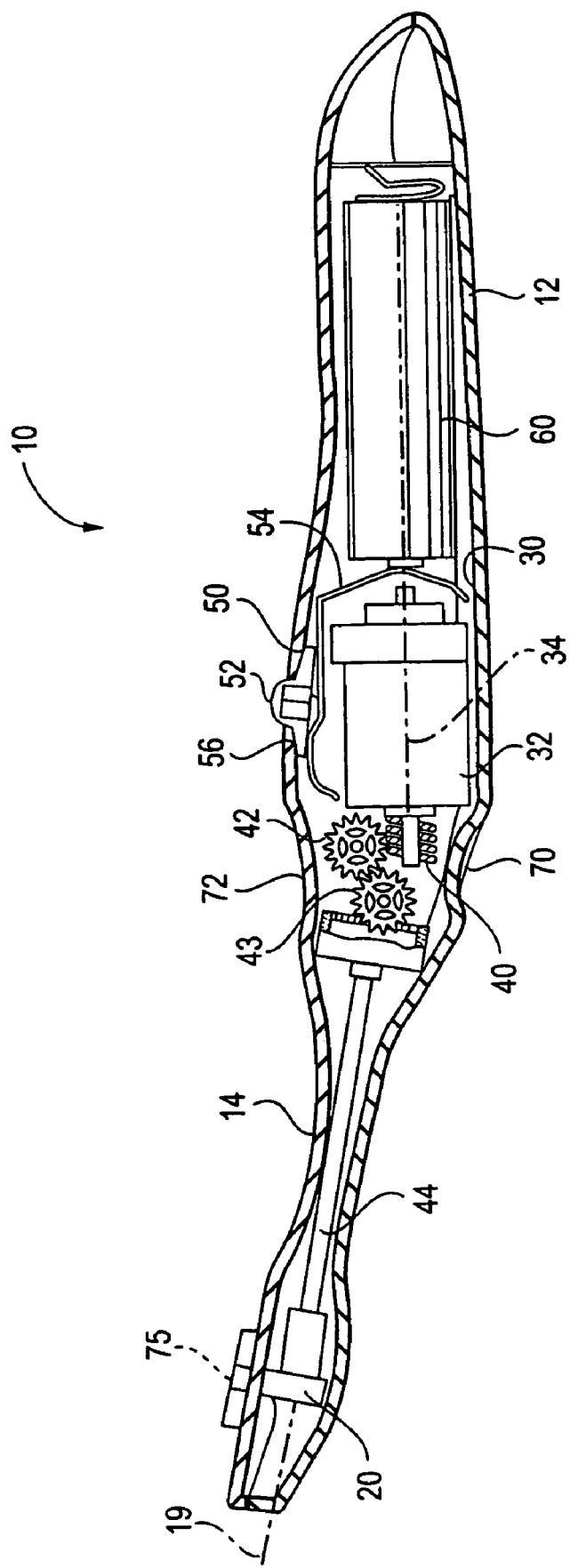
FIG. 3 is a cross-sectional side elevational view of the electric toothbrush of FIG. 1.

As shown in FIG. 3, the handle 12 further includes a hollow portion 30 which houses a motor 32. The motor 32 powers the moving bristle holder 20 through a rotatable shaft 44. A gearing arrangement is operatively interconnected between the shaft 44 and the motor 32. The gearing arrangement includes a worm gear 40 and a pair of step gears 42, 43. The motor 32 is operatively connected to the worm gear 40. Step gear 42 is operatively connected to step gear 43 and the worm gear 40. A light emitting element 75 is provided that is disposed in the interior of the moving bristle holder 20. As used herein, the term "light-emitting" element is intended to refer to an element that converts electrical energy into light, as opposed to an element that merely conducts or transmits light, such as a fiber optic cable or wire. An example of a light-emitting element used in the present invention is a light emitting diode or LED. As used herein, the term "light" is intended to encompass the spectrum of both visible and non-visible (e.g., ultraviolet and infra-red) light. This spectrum may extend from light having a dominant or centroid wavelength of about 10 nm (far ultraviolet) to light having a centroid wavelength of $10^6$ nm (infrared), although visible light having a centroid wavelength between about 370 nm and about 770 nm is typical. As used herein, the term "centroid wavelength" is intended to refer to the wavelength which represents the perceived color of the light. This may be different than the peak wavelength which is the wavelength at which the radiant intensity of the light-emitting element is maximum.

Figure 4:
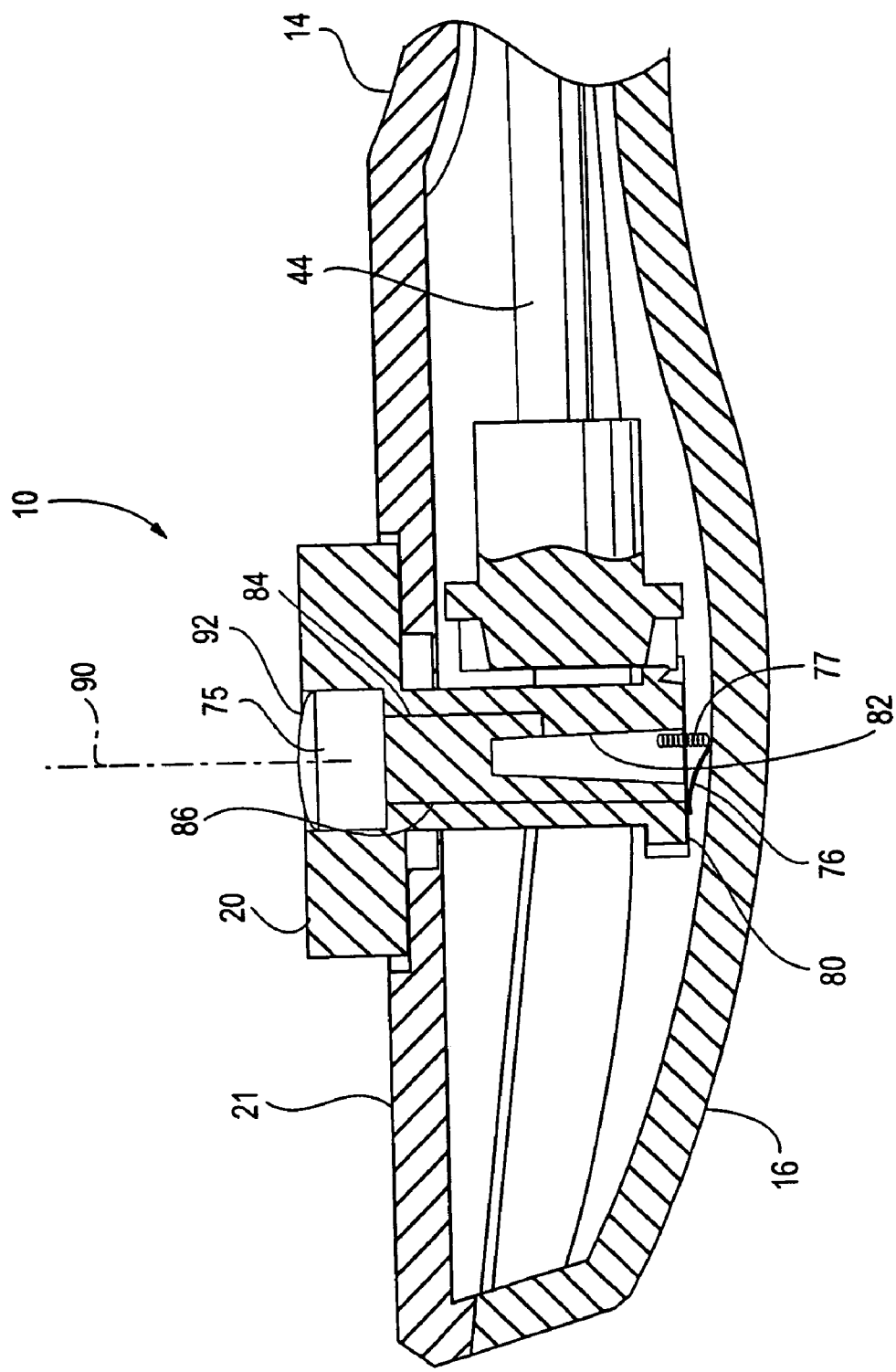
FIG. 4 is a detailed partial cross-sectional view of the head of the toothbrush of FIG. 1.

Referring to FIG. 4, the light-emitting element 75 is mounted or secured to the moving bristle holder 20 so that element 75 moves with moving bristle holder 20. Electric power is provided to the light-emitting element 75 by the use of a pair of electrical contacts 76 and 77 that slidingly contact dedicated contact portions defined along the underside of the moving bristle holder 20, as shown by way of example in FIG. 4. Electrical conductors or wires (not shown) may be provided from the switch 50 and power source 60 to the contacts 76 and 77 for conducting electricity from the power source to the light-emitting element. The wires may extend from the handle 12 through the neck 14 to the head 16. The wires are disposed adjacent the interior wall of the neck 14 so that they do not interfere with the movement of the shaft 44. Alternatively, the wires may be embedded within the neck 14. The electrical conductors may include conductors 54 and 58 as shown in FIG. 3.

Referring again to FIG. 3, a switch 50 is provided to control operation of the illuminated electric toothbrush and is operatively connected to the motor 32. The switch 50 is also configured to operate the one or more light-emitting elements of the toothbrush. Such operation is for instance, momentary or continuous. When the switch 50 is closed, a circuit is completed between a battery 60 provided within the hollow portion 30 of the handle 10 and the motor 32 and light-emitting element 75. A protective cover 52 may be provided over an aperture 56 defined in the handle 12, through which the switch 50 can be actuated.

It is contemplated that circular electrically conductive contact regions 80 and 82 in FIG. 4 could be provided along the exterior of the moving bristle holder 20, which regions would be in electrical communication with the pair of fixed contacts 76 and 77 provided within the interior of the head. The electrically conductive contact regions 80 and 82 are insulated from each other by a non-conductive material. Electrical leads 84 and 86 can be provided from the electrically conductive contact regions to the light-emitting element. FIG. 4 illustrates the light-emitting element 75 disposed on or within the moving bristle holder 20. In this embodiment the light-emitting element 75 is fixedly attached to the moving bristle holder 20 and therefore moves with the bristle holder 20. The tip of the light-emitting element 75 is flush with the top surface 21 of the moving bristle holder 20, although it may extend above the top surface 21 if desired. A transparent protective shield or cap 92 can be used as shown. Additional light-emitting elements can be provided in or on the static bristle holders 22.

Figure 4A:
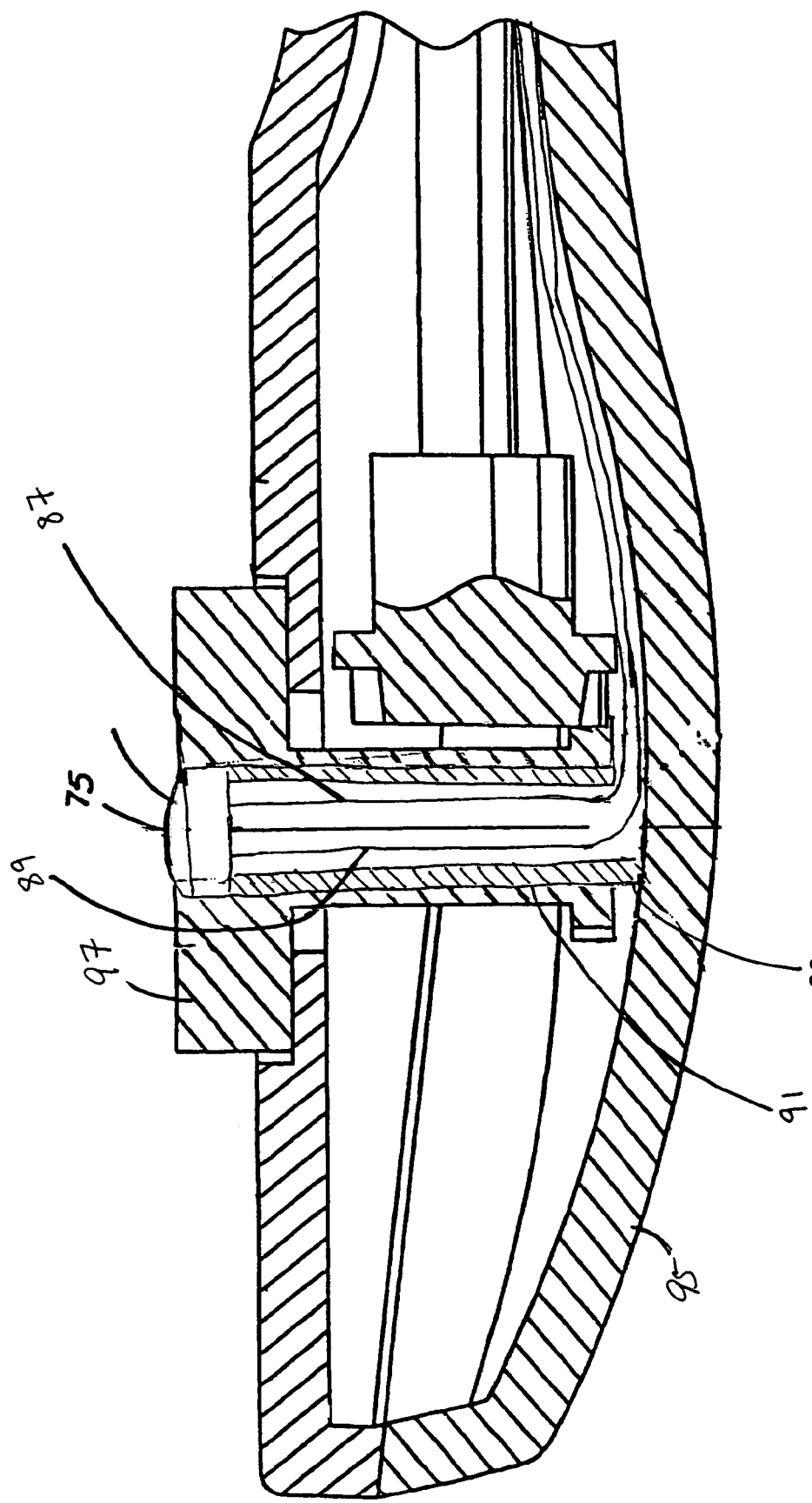
FIG. 4a is a cross-sectional side view of the head of an embodiment of the present invention.

FIG. 4a shows a stationary LED 75 that is connected to a pillar 91 that is stationary and fixed to the head 95 at 93 of the toothbrush. The moving bristle holder 97 oscillates or rotates around the stationary LED 75. The positive lead 87 and the negative lead 89 can run from the LED 75 through the pillar 91 and then down the length of the head 95 of the toothbrush to the power source (not shown).

Figure 5:
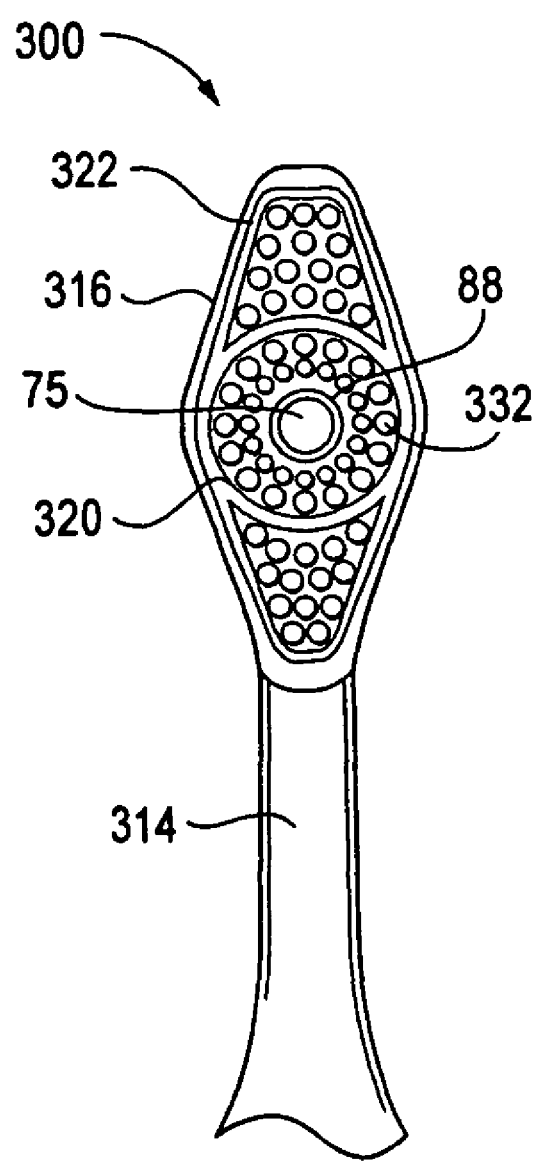
FIG. 5 is a partial front elevational view of a head and neck of an embodiment of the present invention.

In another embodiment illustrated in FIG. 5, a toothbrush 300 is provided having a head 316 and a neck 314. The head includes one or more regions of static bristles 322 and a moving bristle holder 320. The moving bristle holder 320 includes tufts of bristles 332. A light-emitting element 75 is disposed within an aperture or hole 88 that extends through the moving bristle holder 320. The light-emitting element 75 is stationary and the moving bristle holder 320 oscillates or rotates about the stationary light-emitting element 75. In this embodiment, the light-emitting element 75 is fixedly secured to the head 316. The light-emitting element 75 might extend partially through the hole 88 or it may be disposed below the lower surface of the moving bristle holder 320 so that it is completely contained within the head 316. The centerline or axis of the light-emitting element 75 may also be the axis of rotation or oscillation for the moving bristle holder 320.

Figure 6:
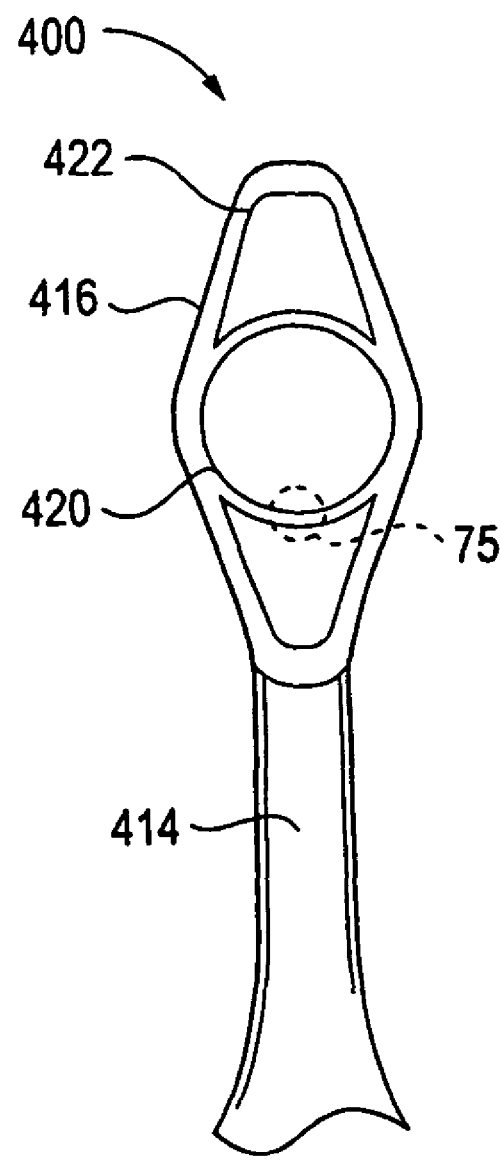
FIG. 6 is a partial front elevational view of a head and neck of an embodiment of the present invention.

FIG. 6 illustrates another toothbrush 400 having a head 416 and neck 414 as previously described. The toothbrush 400 may further comprise the light-emitting element 75 within the interior of the head 416 and utilize one or more regions of the head that are transparent or translucent to reveal the light from element 75, such as regions 422 and 420.

When the light-emitting element is disposed within the head, the light-emitting element may be placed so that it is between bristle holders and not aligned with an axis of rotation/oscillation of a moving bristle holder, as shown by way of example in FIG. 6, wherein the bristles have been deleted for clarity.

In each of the above-described embodiments, the light-emitting element is disposed in, on, below or directly adjacent the moving and/or static bristle holders so that the light is directed onto the brushing area as efficiently as possible. Further, the light-emitting elements can be arranged so that the principle direction of light emission is generally perpendicular to the top surface of the bristle holders and/or generally parallel to the direction of the bristles of the bristle holder. In other words, the light-emitting element is arranged so that the centerline 90 of the light-emitting element is generally perpendicular to the top surface of the head and/or bristle holder, as best seen in FIG. 4. The centerline 90 typically passes through the lens 92 or aperture of the light-emitting element. When the light-emitting element is disposed within, on, or below a moving and/or static bristle holder, a cylindrical region or volume about the centerline 90 of the light-emitting element can be substantially devoid of bristles so that light is transmitted to the brushing surface without interference from the bristles. Generally, the diameter of the cylindrical volume that can be substantially devoid of bristles is greater than about 0.6, 0.7, 0.8, 0.9 and/or 1.0 cm and/or less than about 2.0, 1.5, 1.4, 1.3, 1.2, 1.1, and/or 1.0 cm. The moving bristle holder may have at least one ring of bristles that encircle the light-emitting element, as shown by way of example in FIG. 5.

Figure 7:
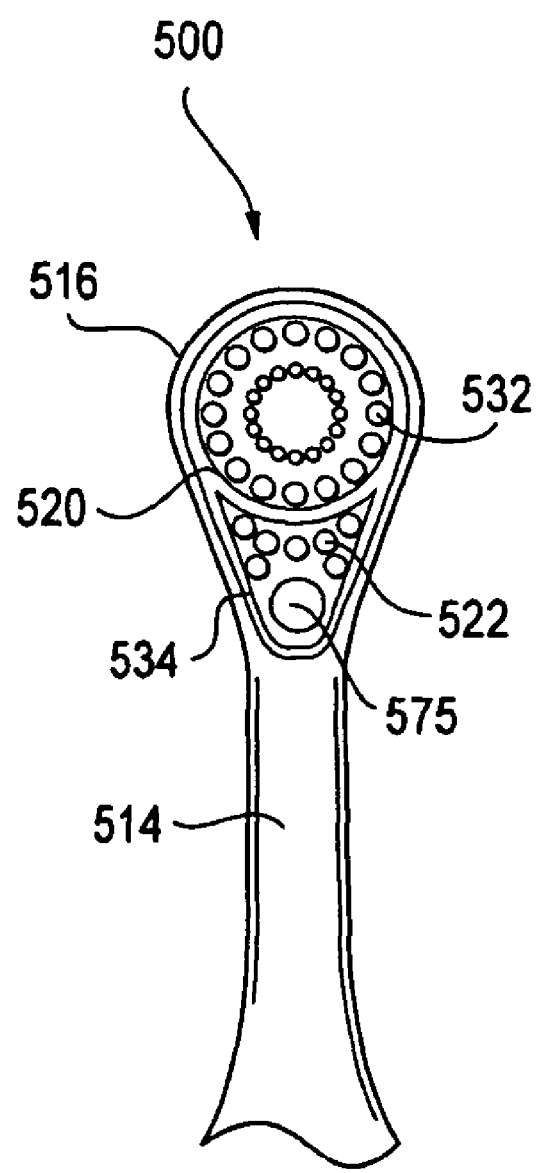
FIG. 7 is a partial front elevational view of a head and neck of an embodiment of the present invention.

FIGS. 7-10 illustrate other head, bristle holder and bristle configurations for illuminated electric toothbrushes, all of which contain one or more lights or light-emitting elements. FIG. 7 illustrates a toothbrush 500 having a head 516 and a neck 514. It will be appreciated that the neck 514 extends between the head 516 and a handle of the toothbrush (not shown). Disposed on the head 516 is a single moving bristle holder 520 having a plurality of bristles or tufts 532 disposed thereon. Disposed on a second bristle holder 522 is a light-emitting element 575 and optional bristles 534.

Figure 8:
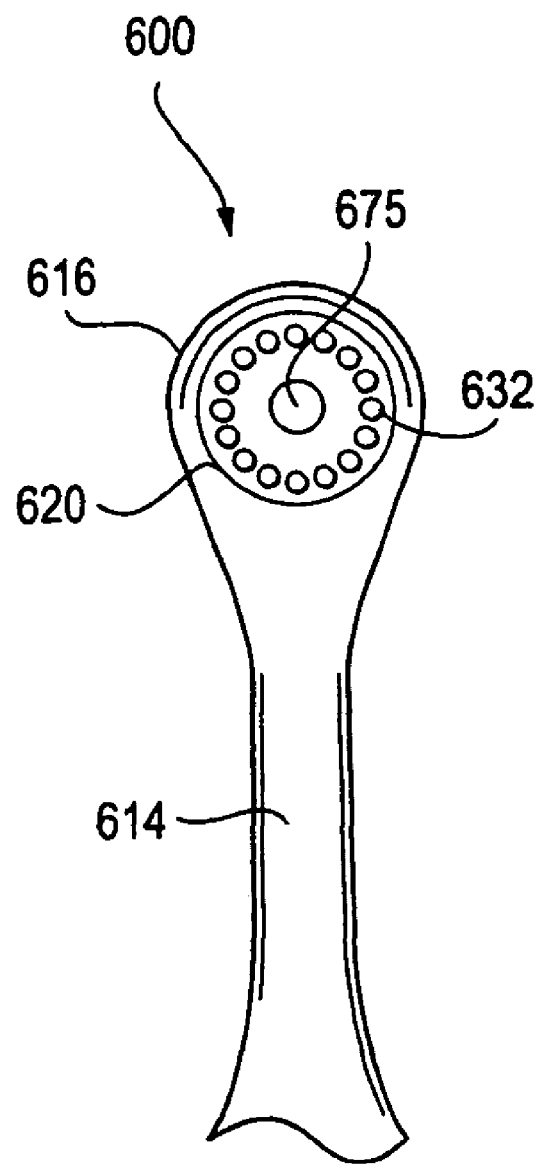
FIG. 8 is a partial front elevational view of a head and neck of an embodiment of the present invention.

FIG. 8 depicts another toothbrush 600 including a head 616 and a neck 614 in accordance with the present invention. The head 616 comprises a single bristle holder 620 having a light-emitting element 675 disposed therein and bristles 632.

Figure 9:
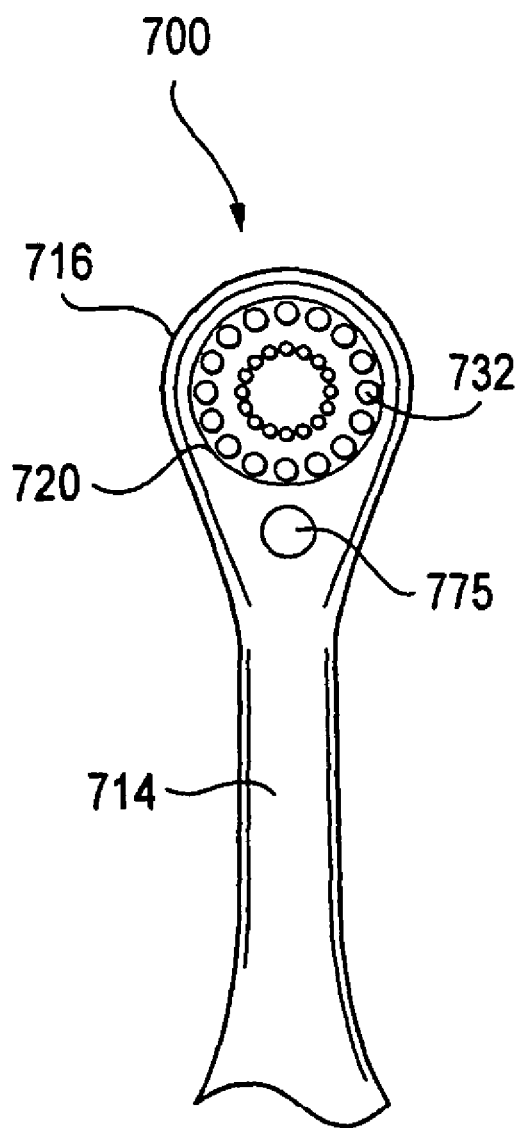
FIG. 9 is a partial front elevational view of a head and neck of an embodiment of the present invention.

FIG. 9 depicts yet another toothbrush including a head 716 and a neck 714 having a single bristle holder 720 disposed thereon. Holder 720 includes bristles 732. A light-emitting element 775 is disposed adjacent the bristle holder 720 on the head 716. The light-emitting element 775, however, is not disposed on the bristle holder.

Figure 10:
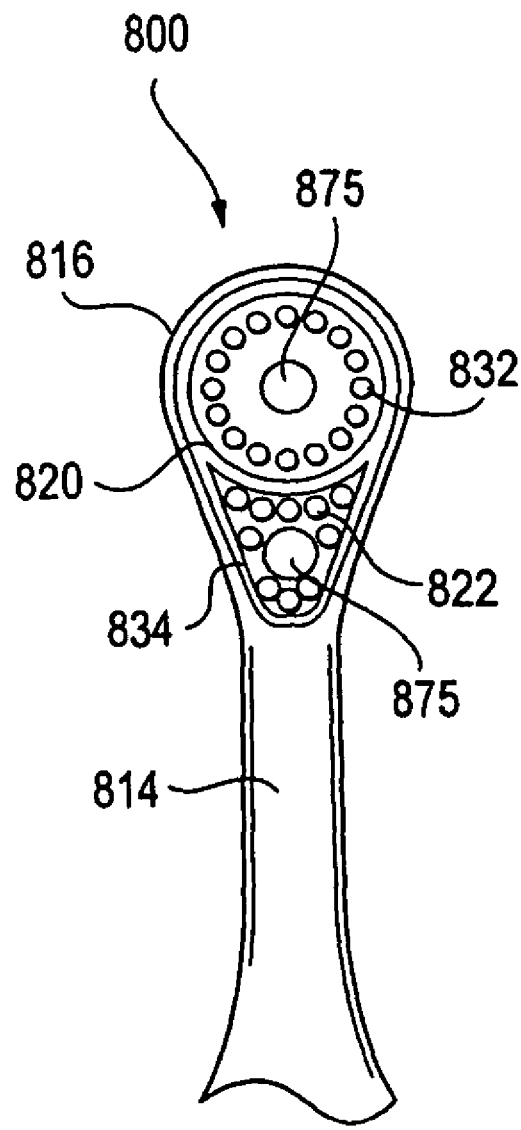
FIG. 10 is a partial front elevational view of a head and neck of an embodiment of the present invention.

FIG. 10 depicts still another toothbrush 800 including a head 816 and a neck 814 having a first bristle holder 820 that moves and a second bristle holder 822 that is fixed or stationary. Both bristle holders have light-emitting elements 875 disposed thereon. The first bristle holder 820 has a plurality of bristle tufts 832 that encircle the light-emitting element 875 disposed thereon, and the second bristle holder 822 has a plurality of bristle tufts 834 that encircle the light-emitting element 875 disposed thereon.

Figure 11:
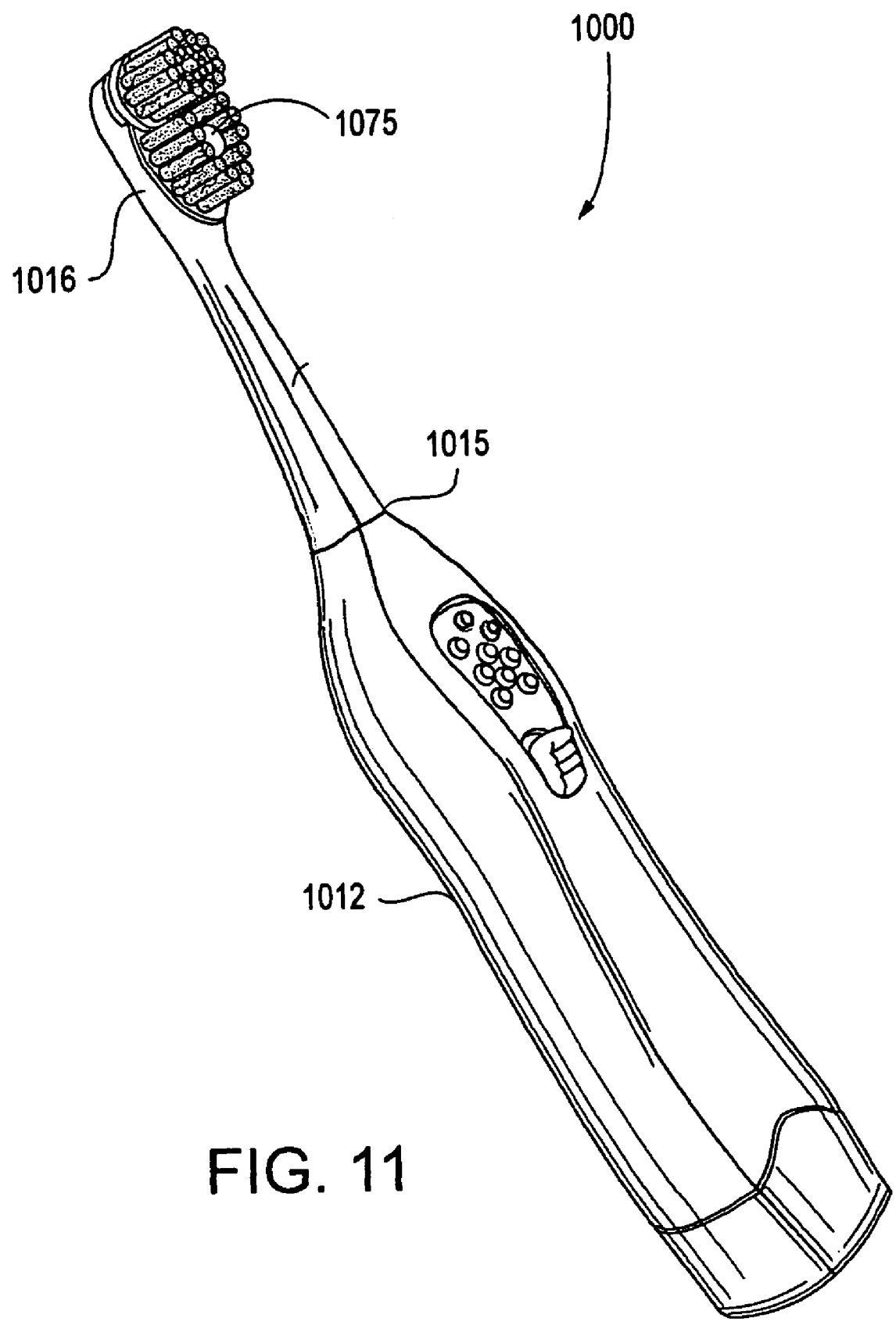
FIG. 11 is a perspective view of an embodiment of the electric toothbrush of the present invention in which the toothbrush includes a head and neck that can be separated from the handle.
Figure 12:
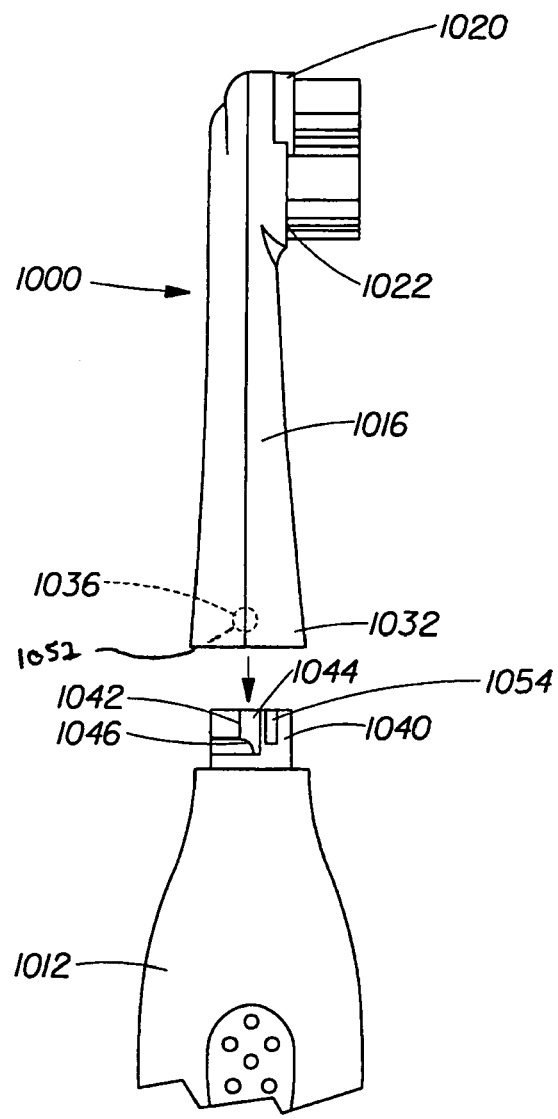
FIGS. 12 and 13 are partial side elevational views illustrating installation of a replaceable head and neck onto a handle or handle portion of the illuminated electric toothbrush of FIG. 11.
Figure 13:
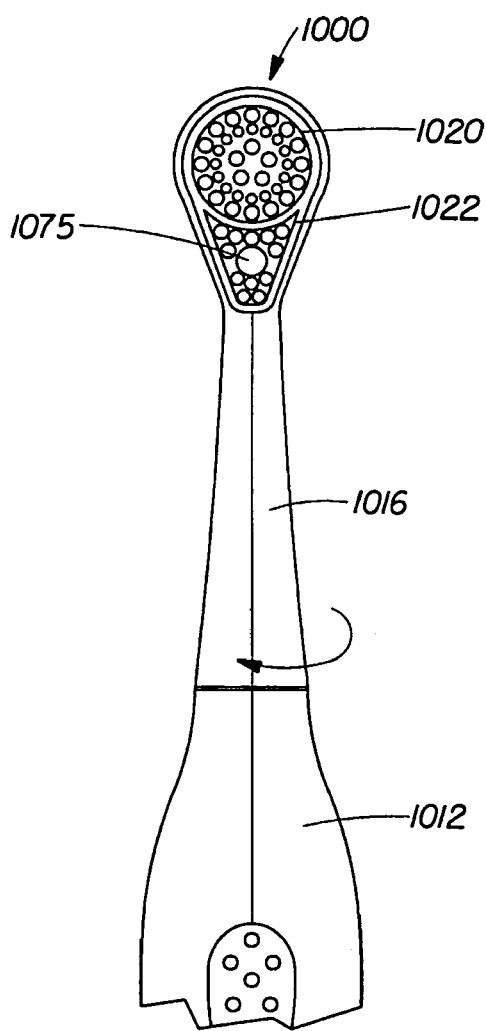

As shown in FIGS. 11-13, and specifically in FIG. 11, another illuminated electric toothbrush 1000 is illustrated having a head and a neck assembly 1016, and a handle 1012. Disposed on the head and neck assembly 1016 is a light-emitting element 1075. The head and neck assembly are releasably connected to the handle 1012 along an engagement interference 1015 and contain corresponding structures for their physical engagement and for establishing electrical communication between the light-emitting element and the power source. Referring now to FIGS. 12 and 13, the head and neck 1016 further includes a moving bristle holder 1020 and a static bristle holder 1022. Disposed on the static bristle holder 1022 is a light emitting element 1075.

The head and neck 1016 has two small pins or projection members 1036 (in phantom) located inside the neck end portion 1032. The small projections are dimensioned to fit into L-shaped slots 1042 or receiving regions defined along a mating end portion 1040 of the handle 1012. The width of the L-shaped slots 1042 is slightly wider than the width of the small projections to enable the L-shaped slots to receive the small projections. The depth of the L-shaped slots is substantially equal to the height of the small projections so that the L-shaped slots can receive the small projections.

To connect the head and neck to the handle, the user aligns the small projections with a top surface 1044 of the L-shaped slots. The user pushes or presses the head and neck 1016 down so that the small projections contact a bottom surface 1046 of the L-shaped slots 1042. When the small projections have contacted the bottom surface 1046 of the L-shaped slots, the user then turns the head and neck 1016 approximately 90 degrees with respect to the handle 1012, thereby locking the head into place, as seen in FIG. 13. A top surface of each of the projections becomes locked under a top surface of each of the L-shaped slots 1042. The user thus exerts a press-and-twist action on the cooperating pins and guide slots to put the head into a fully attached disposition on the handle and realize a locking engagement between the two.

One or more electrical contacts are provided along the mating region of the neck and the handle to provide a releasable electrical connection therebetween. For example, a first set of cooperative electrical contacts representing a positive electrical connection between the handle and neck are disposed within the mating region of the neck and handle and provide electrical communication to the one or more light-emitting elements on the head, such as element 1075 in FIG. 13. A second set of cooperative electrical contacts representing a negative or ground electrical connection is also disposed between the neck and handle. Upon engagement of the neck and handle, the first and second sets of contacts are placed in electrical communication with each other. An exemplary first set of electrical contacts 1052 (in phantom) and 1054 are shown in FIG. 12 that, upon engagement between the head and the handle, place the light-emitting element 1075 in electrical communication with the power source of the electric toothbrush. While the electrical contacts are shown as separate from the pin and slot structures that mechanically interconnect the neck and handle, it is contemplated that the electrical contact 1054 can be disposed at the bottom of the L-shaped slot 1042 while the electrical contact 1052 forms part of the pin 1036 so that when the pin 1036 engages the L-shaped slot, electrical communication is established between the head and the handle. In this embodiment, the pin and L-shaped slot may be provided wholly or partially as a conductive material. The second set (ground) of electrical contacts can be provided in the opposing, similarly arranged slot and pin configuration (not shown) disposed opposite the first pin 1036 and first slot 1042. It is contemplated that a variety of other configurations and techniques may be used to provide electrical power to one or more light-emitting elements disposed on a removable neck and head. For example, spring-biased contacts might be utilized. Further, while the present embodiment has been described with regard to a head and neck that are separable from the handle, it is contemplated that a head that separates from a neck, wherein the neck is fixedly attached to the handle, could also employ electrical connections of the present invention.

Figure 13A:
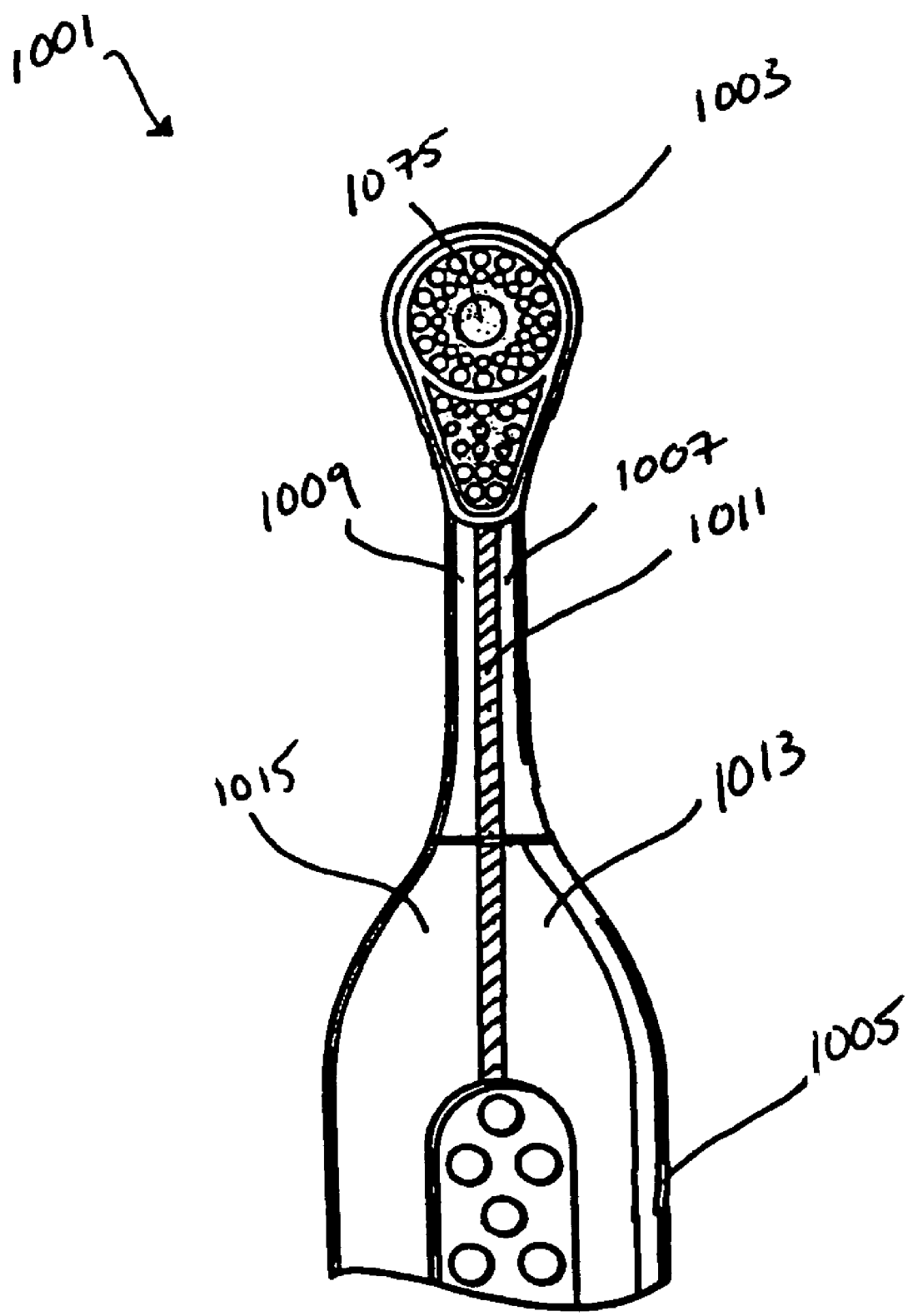
FIGS. 13a and 13b are partial side elevational views illustrating an embodiment of the toothbrush of the present invention in which the toothbrush comprises electrically conductive polymers.
Figure 13B:
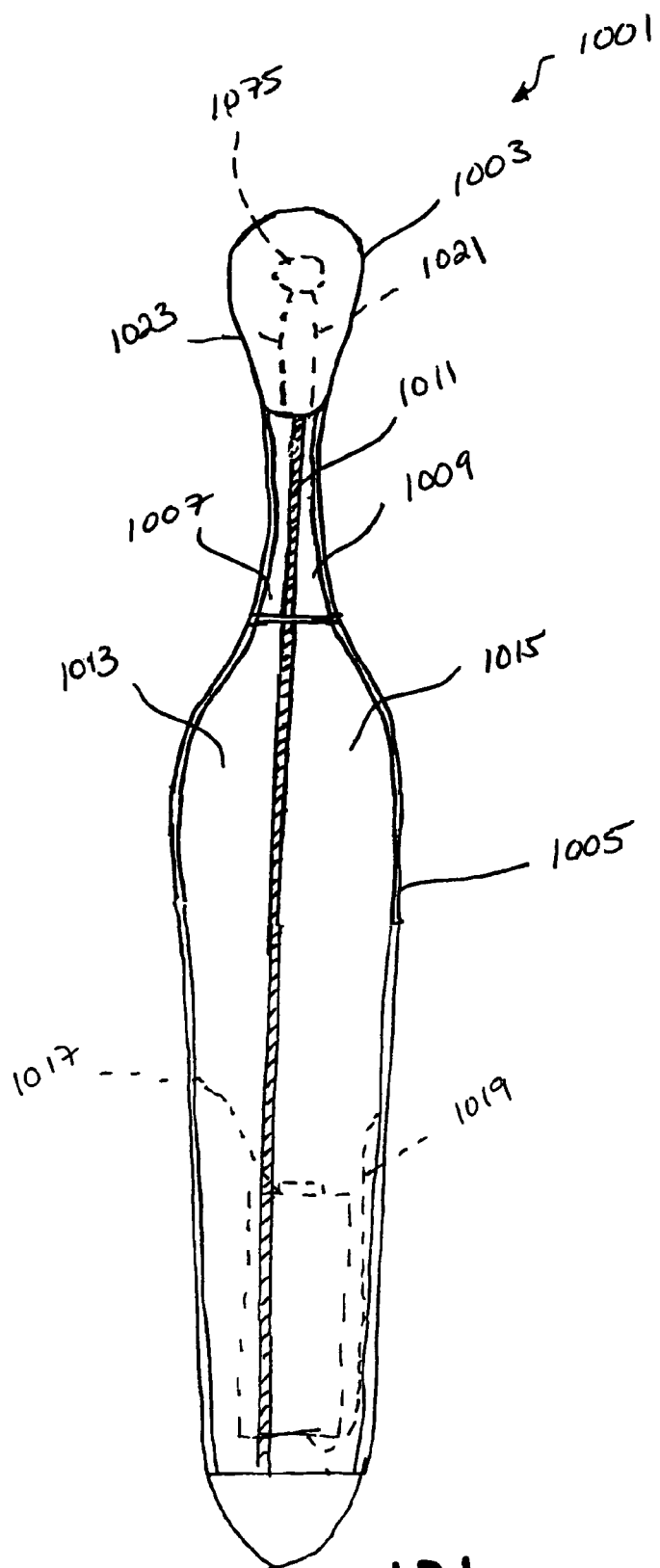

In another embodiment (as shown in FIGS. 13a-b) the head 1003 and handle 1005 of the toothbrush 1001 comprise electrically conductive substrates, including but not limited to metals and/or electrically conductive polymers. One portion 1007 of the head 1003 can comprise a conductive substrate connected with the negative electrode 1023 of the electrically powered element including, but not limited to, LED 1075 and the other portion 1009 of the head 1003 can comprise a conductive substrate connected with a positive electrode 1021 of the LED 1075. These electrically conductive portions of the head can be separated from one another with an insulating material 1011. These materials can be layered or be pieces that are assembled to form the head. The portions of the toothbrush handle can also comprise electrically conductive substrates, one electrically conductive portion 1013 of the handle being connected to positive pole 1017 of the battery and another electrically conductive portion 1015 of the handle being connected to the negative pole 1019 of the battery. When the head and body are joined, the electrically conductive portion of the handle connected with the positive pole of the battery meets the electrically conductive portion of the head connected with the positive electrode of the electrical element disposed on the head, including LED 1075 whereas the electrically conductive portion of the handle connected with the negative pole of the battery meets the electrically conductive portion of the head connected with the negative pole of the electrical element disposed on the head, including LED 1075, thereby completing the electrical connection. In another embodiment the portions of the handle 1027 and the head 1025 that contact each other when the head and handle are engaged may comprise a layer of polymer comprising electrically conductive properties. This layer can be divided into electrically conductive portions 1035, 1031, 1043, 1039 having an insulating material 1037, 1033, 1045, 1041 between the portions. When the head and body are joined, the electrically conductive portion of the handle 1043 connected with the positive pole of the battery meets the electrically conductive portion of the head 1035 connected with the positive electrode of the electrical element disposed on the head, including LED 1075 whereas the electrically conductive portion of the handle 1039 connected with the negative pole of the battery meets the electrically conductive portion of the head 1031 connected with the negative pole of the electrical element disposed on the head, including LED 1075, thereby completing the electrical connection. The electrically conductive polymer layer can be joined to the battery and/or the LED via wires which are molded into the electrically conductive polymer layer.

Figures 13C, 13D:
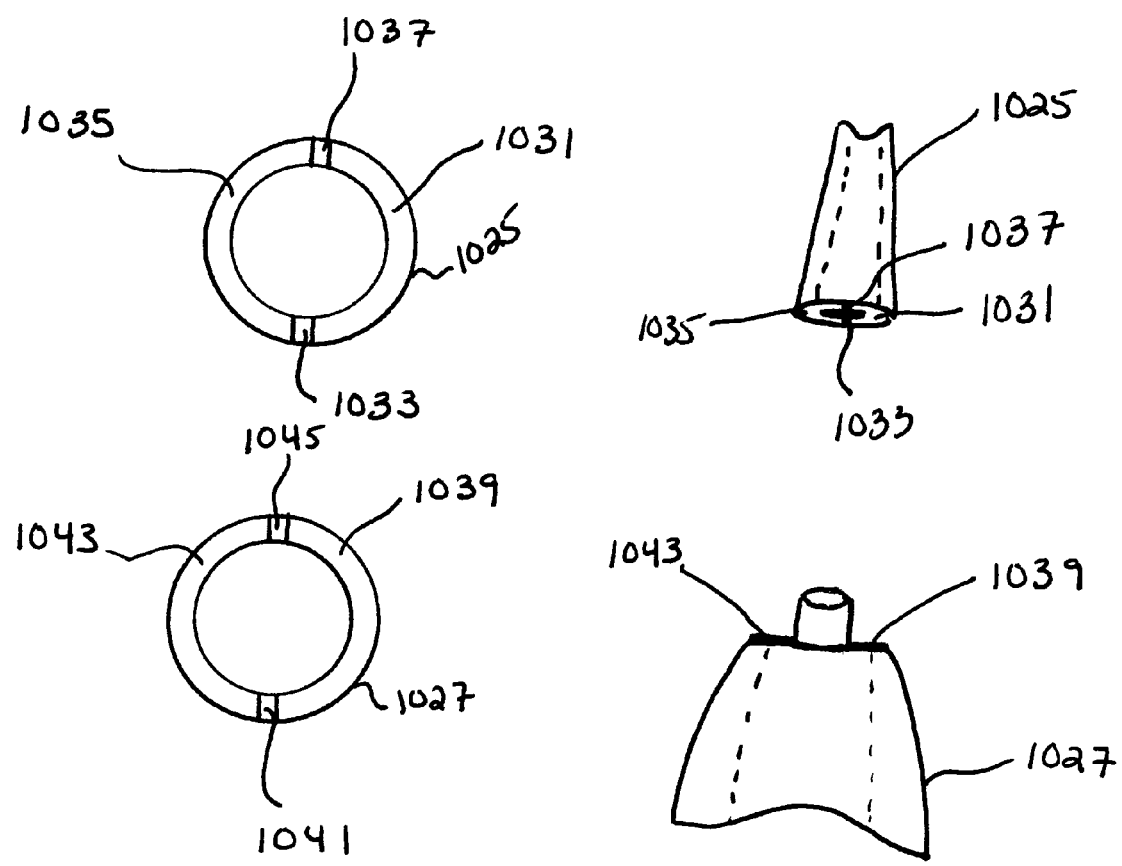
FIG. 13c is an exploded view illustrating an embodiment of the toothbrush of the present invention in which the toothbrush comprises electrically conductive polymers.
FIG. 13d is a partial side view illustrating an embodiment of the toothbrush of the present invention in which the toothbrush comprises electrically conductive polymers.

Additionally, the conductive substrate may also comprise conductive particles. When this conductive substrate is quiescent it is not conductive, and can serve as an insulator and/or a seal. However, when the conductive substrate is compressed the conductive particles are condensed thereby resulting in an electrically conductive substrate. This substrate can be a polymer layer 1043 and 1039 on the connecting portions of the toothbrush as shown in FIGS. 13c and 13d. Finally, a connector comprising any combination of toothbrush portions made from conductive substrates and/or regular electrical contacts is contemplated. For example, one component of the connector can be the head comprising a conductive polymer and an insulating layer between the electrically conductive portions of the head, and the mating part can be standard contacts comprising metal disposed on or in the handle of the toothbrush.

It will be appreciated that the connector assemblies described herein may include any number of contacts. As sometimes referred to herein, a contact may be designated as a "positive" or "(+)" contact. And, another contact may be designated as a "negative" or "(−)" contact. Those skilled in the art will appreciate that this terminology refers to the relative electrical potential of the contacts and such designation is used to maintain proper electrical connection between the power supply, i.e. battery, and the electrically powered elements provided on the toothbrush and/or head. Such terminology and its use herein shall not limit the type or connection used for an electrically powered elements. For example, certain light emitting elements may produce or emit light regardless of their connection to a power supply or power circuit.

Furthermore, it will also be understood that the contacts may be configured on or within the different portions of the toothbrushes in a variety of different fashions. For example, the present invention includes, but is not limited to, providing a positive (+) and negative (−) set of contacts on the head, and providing another set of positive (+) and negative (−) contacts on the handle, such that upon engagement of the head and handle, the respective positive (+) contacts are placed in electrical communication with each other and the respective negative (−) contacts are placed in electrical communication with each other. It is also contemplated to provide three or more positive (+) contacts, for providing multiple electrical pathways such as for multiple electrically powered elements on a brush head, and two negative (−) contacts that provide a single or common "ground" for the collection of electrically powered elements. Alternately, multiple electrically powered elements can be powered using a single electrical circuit using two positive contacts and two negative contacts along the region at which electrical severance occurs. The noted contacts, or sets of contacts, as will be appreciated, can be arranged on, about, or within the toothbrushes of the invention in any configuration.

The contact assemblies described herein may also be in a variety of forms. For example, a set or a plurality of contacts can be incorporated or formed into a single assembly. One such assembly can be incorporated on or within one portion of the toothbrush, such as the head, and another assembly can be incorporated on or within a corresponding other portion of the toothbrush, such as the handle. Upon assembly of the noted portions, the contact assemblies are placed in electrical communication. The contact assemblies, once placed in electrical communication can provide multiple electrical connections between electric conductors, for multiple electric circuits, pathways, etc.

Figure 15:
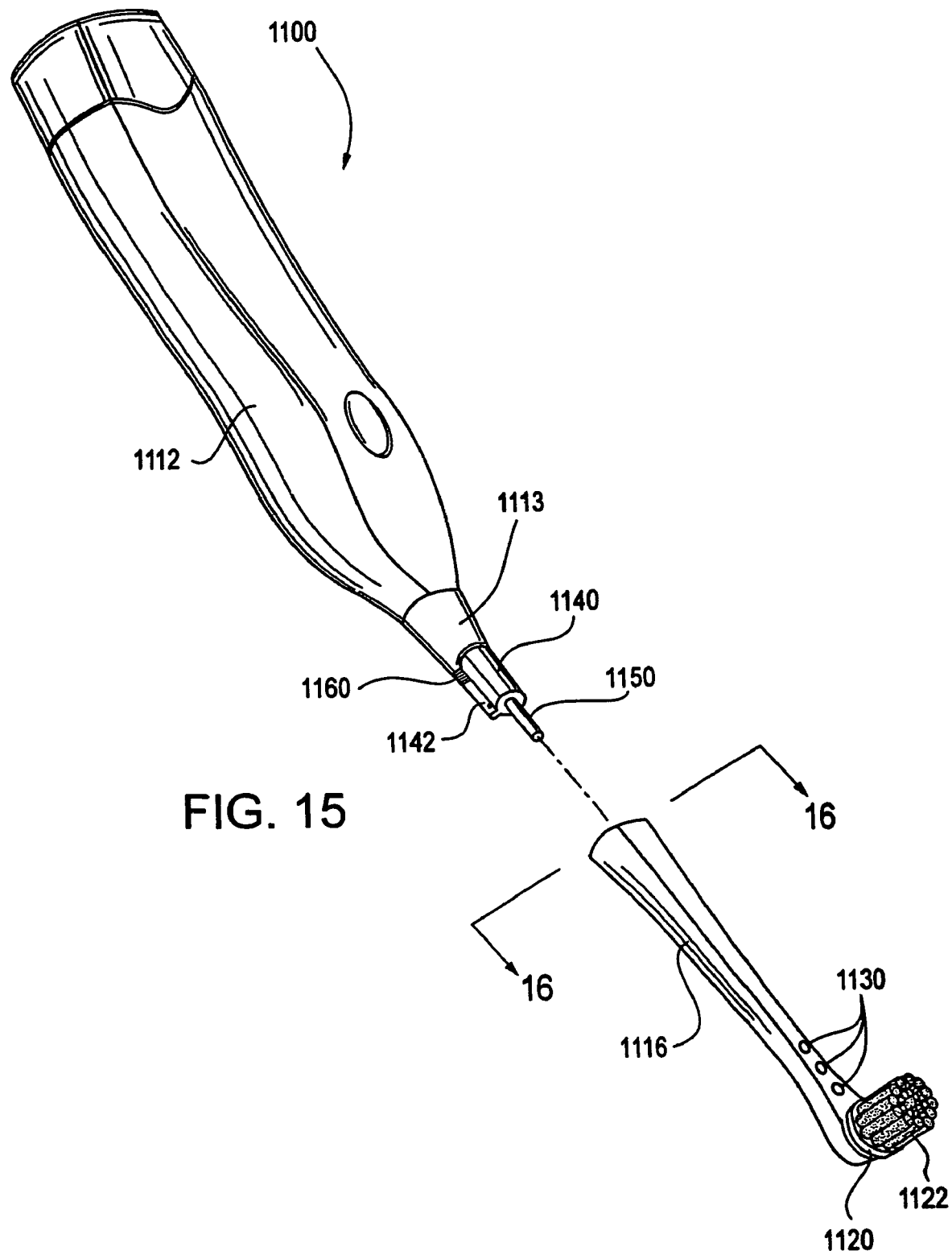
FIG. 15 is a partial exploded view illustrating attachment of a head and neck assembly to a handle or handle portion a toothbrush in accordance with the present invention.
Figure 16:
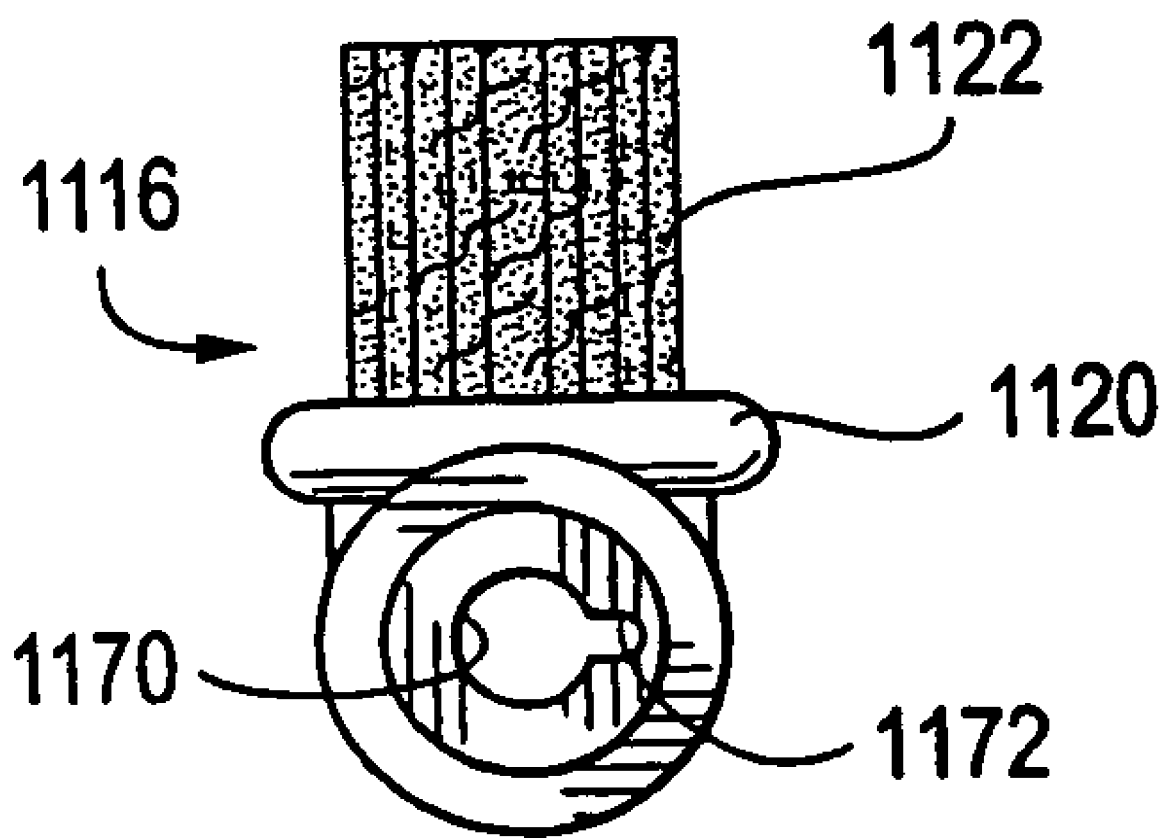
FIG. 16 is an end view of the head and neck assembly depicted in FIG. 15.

FIGS. 15 and 16 illustrate another embodiment toothbrush 1100 in accordance with the present invention. The toothbrush 1100 includes a handle 1112 and a head assembly 1116 which is removable from the handle 1112. The head 1116 includes a movable bristle carrier 1120 having a plurality of bristles 1122 disposed and supported thereon. The head 1116 further includes a plurality of light-emitting elements 1120 which require a source of electrical power. The handle 1112 defines an engagement region generally at one of its ends, and in particular, includes a member 1140 which extends outward from an end 1113 of the handle 1112 and generally colinear with the longitudinal axis of the handle 1112. The member 1140 surrounds a portion of a drive shaft 1150 also projecting outward from the handle 1112. The member 1140 includes a rail 1142 projecting radially (or laterally) outward from the member 1140. The rail 1142 extends along the length, or substantially so, of the member 1140. Disposed along at least a portion of the rail 1142 is an electrically conductive contact 1160.

FIG. 16 is an end view of the head 1116, and reveals a receiving region 1170 defined within a generally hollow interior defined in the head 1116, and accessible from an end of the head 1116. The receiving region 1170 is sized and oriented to engage the member 1140 of the handle 1112 upon attaching, or re-attaching, the head 1116 to the handle 1112. It will be appreciated that a corresponding drive shaft receiving region is included in the head 1116 to enable transfer of motion of the drive shaft 1150 to the movable bristle carrier 1120. Also disposed within the receiving region 1170 is an electrically conductive contact 1172. The contact 1172 is disposed within the receiving region 1170 such that upon attachment of the head 116 to the handle 112, the contact 1172 is in electrical communication with the contact 1160.

Figure 15C:
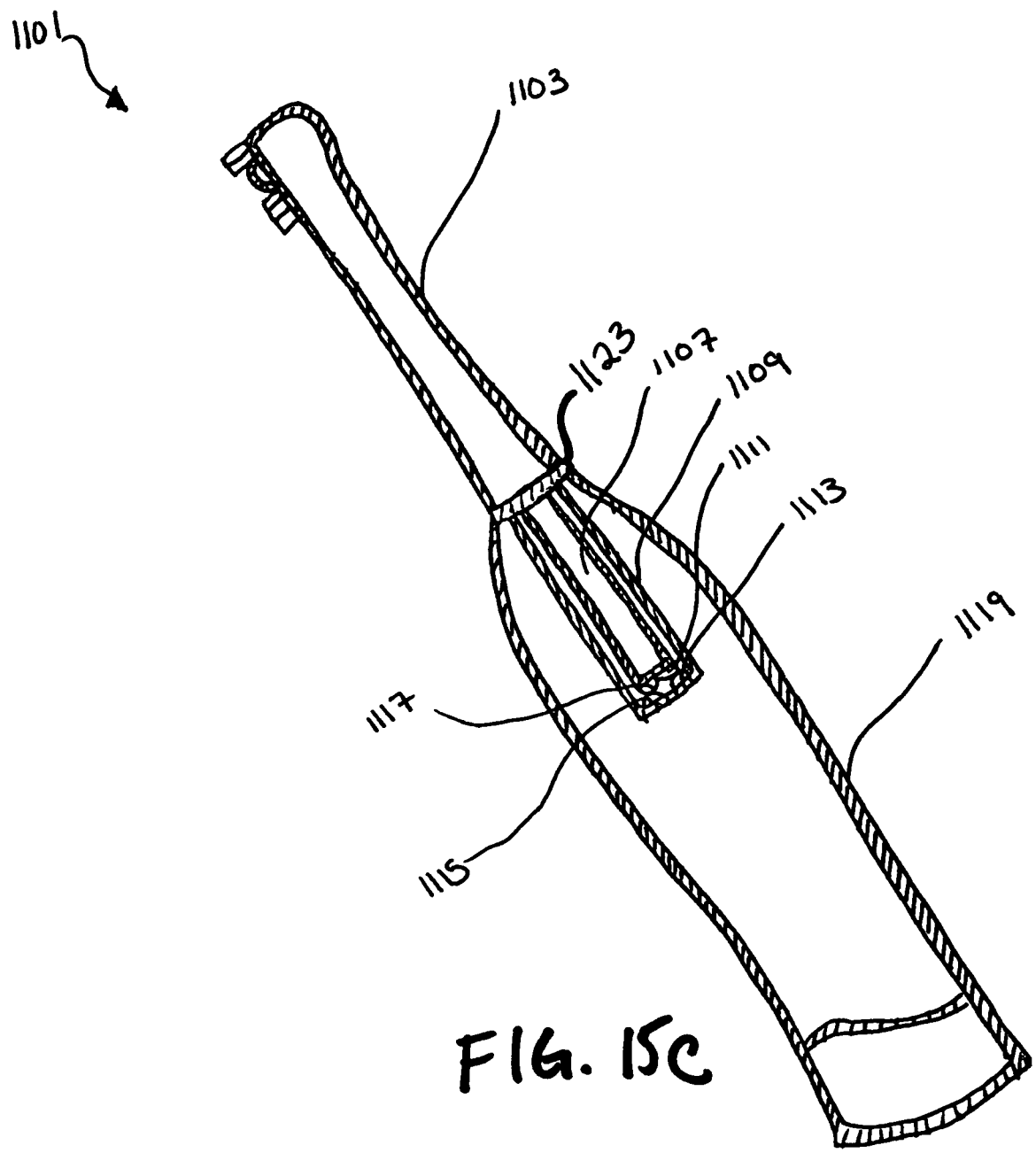
FIG. 15c is a detailed cross sectional view of the electric toothbrush illustrating engagement of the head and handle of the toothbrush.
Figure 15D:
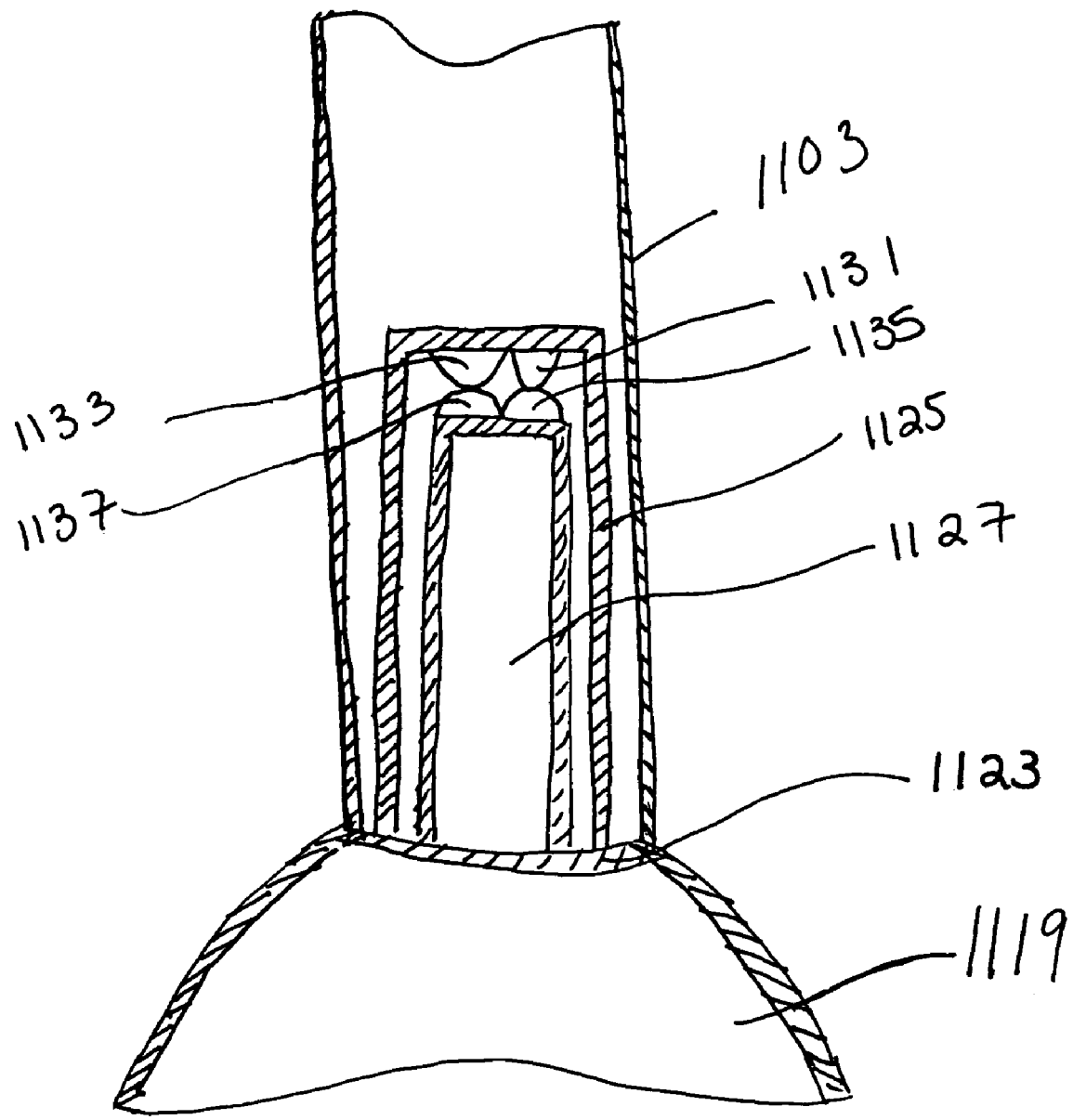
FIG. 15d is a partial exploded cross sectional view illustrating the head and neck portion of a toothbrush in accordance with the present invention.

FIGS. 15a-c illustrate an embodiment of the toothbrush 1101 in accordance with the present invention. The toothbrush 1101 comprises a handle 1119, and a removable head 1103. The head includes an engagement member 1107 that cooperates with a receiving region 1109 defined within the handle 1119. Disposed on the engagement member 1107 are components of an electrical connector, such as contacts 1111 and 1117 (as shown in FIG. 15b) upon which engagement of the head to the handle (as shown in FIG. 15c) is placed in electrical communication with other components of the connector such as contacts 1115 and 1125 disposed within the receiving region of the handle 1119. When the head is assembled with the handle (as shown in FIG. 15c), the head is placed in electrical communication with the handle, and the head components of the connector are received within the handle 1119; thereby protected from contact with water. It is further contemplated that the handle components of the electrical connector can be received within the head of toothbrush (as shown in FIG. 15d). The head includes a receiving region 1125 and the connector components disposed on the handle are located on an engagement member 1127 extending from the handle. Disposed within the receiving region of the head are components of an electrical connector, such as contacts 1131 and 1133. Upon engagement of the head 1103 to the handle 1119 the electrical contacts 1131 and 1333, disposed within the receiving region 1125, are placed in electrical communication with the handle components of the connector, electrical contacts 1135 and 1137, disposed on the engagement member 1127, and the head is placed in electrical communication with the handle. A seal, including but not limited to an o-ring seal 1123, can be used at the joint area between the handle 1119 and the head 1103 to further prevent moisture from entering the interior cavities of the electric toothbrush and interfering with the electrical communication between the contacts.

Figure 17:
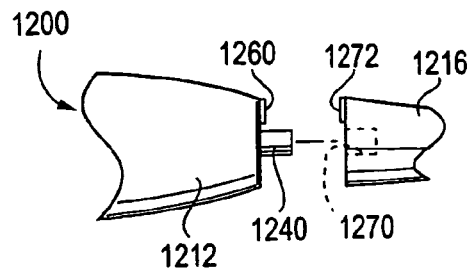
FIG. 17 is a detailed partial exploded view illustrating attachment of a head and neck assembly to a handle or handle portion of an toothbrush in accordance with the present invention.
Figure 18:
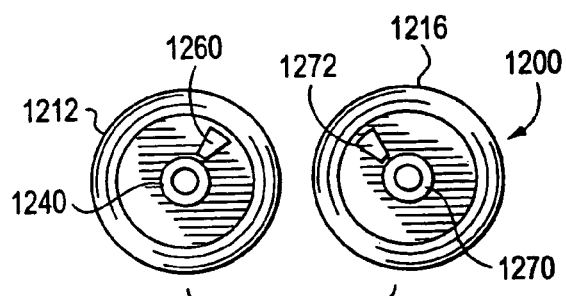
FIG. 18 is an end view of the handle portion and the head and neck assembly of the embodiment illustrated in FIG. 17.

FIGS. 17 and 18 illustrate another embodiment toothbrush 1200 in accordance with the present invention. The toothbrush 1200 comprises a handle 1212 and a removable head 1216. The handle 1212 includes an engagement member 1240 that cooperates with a receiving region 1270 defined within the head 1216. Disposed on an end of the handle is a contact 1260 which, upon engagement of the head 1216 to the handle 1212, is placed in electrical communication with another electrically conductive contact 1272 disposed on a mating end of the head 1216. FIG. 18 illustrates a configuration for the contacts 1260 and 1272. It will be understood that one or more alignment members can be provided along the region of engagement between the handle 1212 and the head 1216 to ensure proper positioning, e.g. rotation, of the head 1216 with respect to the handle 1212.

Figure 19:
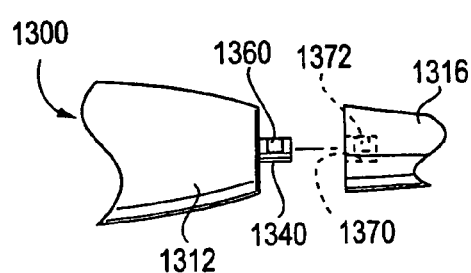
FIG. 19 is a partial exploded view illustrating attachment of a head and neck assembly to a handle or handle portion a toothbrush in accordance with the present invention.

FIG. 19 depicts another embodiment toothbrush 1300 in accordance with the present invention. The toothbrush 1300 includes a handle 1312 and a head 1316 which are selectively engageable with each other. The handle 1312 includes a cylindrical member 1360 disposed along an outer region of the member 1360. Provided along a region of the member 1340 is a contact 1360. The head 1316 defines an interior receiving region 1370 sized and oriented to engage the member 1340. Provided within the region 1370 is another contact 1372. Upon engagement of the head 1316 with the handle 1312, the contacts 1360 and 1372 are in electrical communication, and provide an electrical path or conduit between the head 1316 and the handle 1312.

Figure 20:
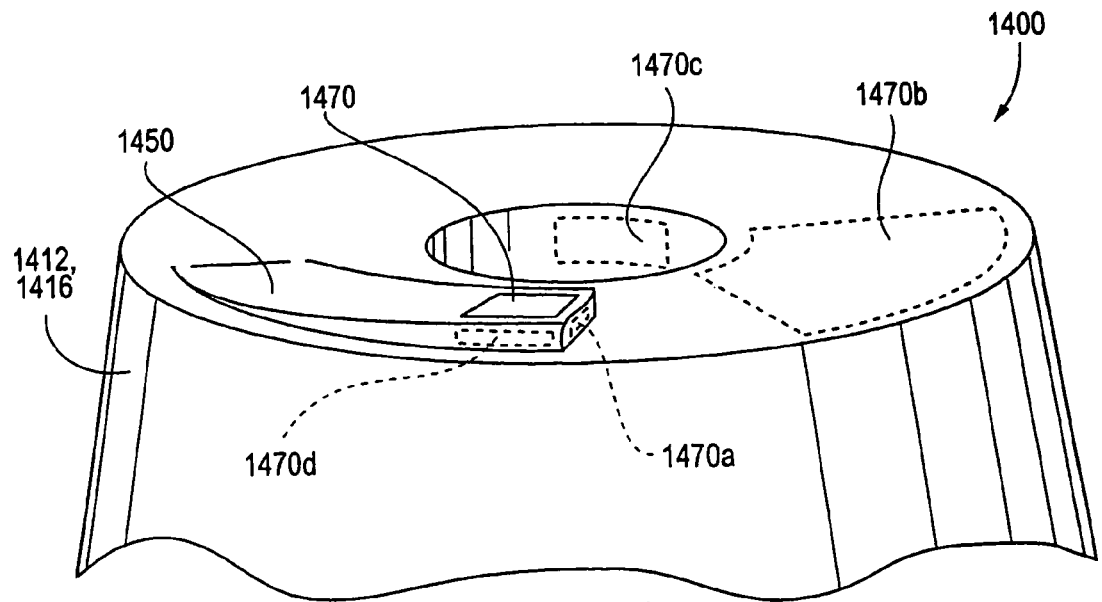
FIG. 20 is a detailed perspective view of a portion of an electrical connector in accordance with the present invention.

FIG. 20 illustrates a portion of another embodiment toothbrush 1400 in accordance with the present invention. Depicted is either an engagement region of a handle 1412 or a head 1416 of the toothbrush 1400. Disposed on the engagement region, is a ramp or incline member 1450 having an electrically conductive contact 1470 disposed thereon. The contact 1470 may be located on the inclined surface of the member 1450, or may be positioned elsewhere on the engagement region such as, but not limited to, regions shown in FIG. 20 with dashed lines depicting alternate positions of contact 1470, i.e. 1470a, 1470b, 1470c, and 1470d.

Figure 21:
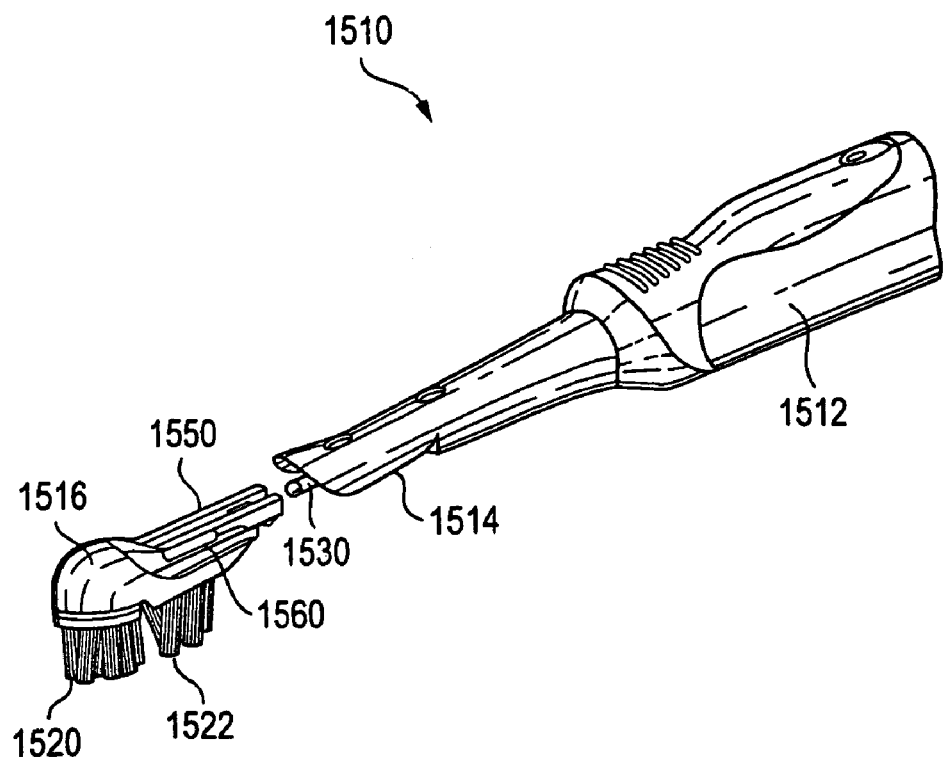
FIG. 21 is a partial exploded view of a toothbrush in accordance with the present invention.
Figure 22:
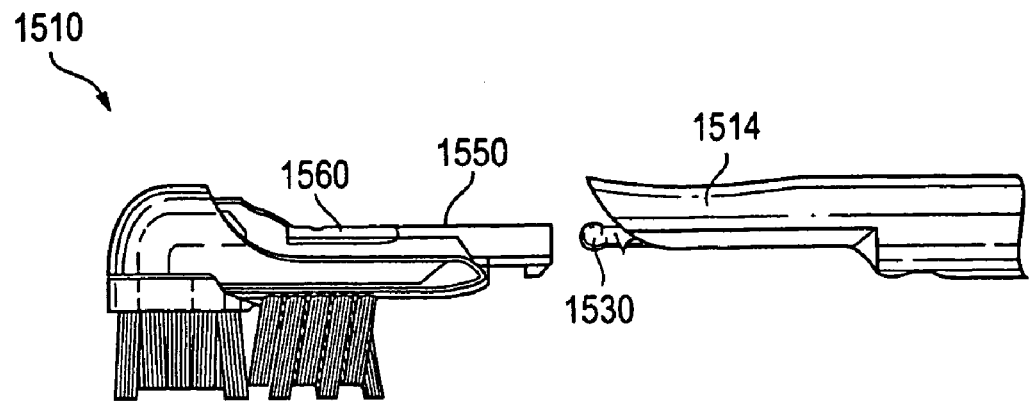
FIG. 22 is a partial detailed side view of a removable head and a neck portion of the toothbrush shown in FIG. 21.
Figure 23:
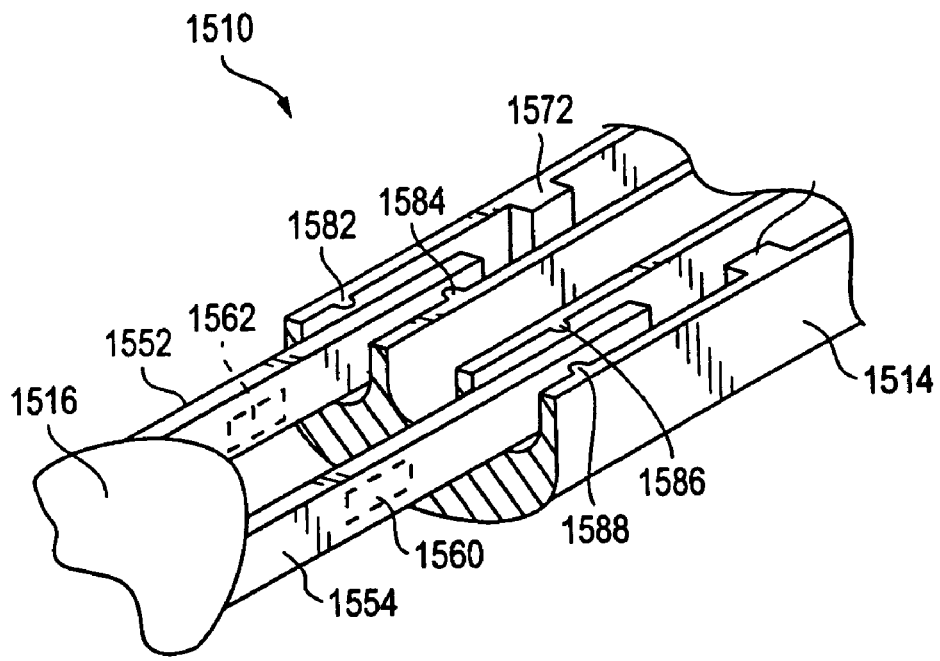
FIG. 23 is a partial sectional view of the toothbrush shown in FIGS. 21 and 22, illustrating engagement of the head and neck portions.

FIGS. 21-23 illustrate another embodiment toothbrush 1510 according to the present invention. The toothbrush 1510 comprises a handle 1512, a neck 1514 projecting from an end of the handle 1512, and a removable head 1516. Mounted on the head 1516 is a movable bristle carrier 1520 having a plurality of bristles projecting therefrom. Disposed between the movable bristle carrier 1520 and the end of the head 1516 to which the neck 1514 attaches, is a plurality of fixed or stationary bristles 1522. It will be understood that the handle 1512 and neck 1514 retain and generally house a motor and drive mechanism as described herein. FIG. 21 illustrates a distal end of the drive shaft 1530 projecting outwardly therefrom. The head 1516 includes one or more electrically powered element such as previously described. The head 1516 engages the neck 1514 by use of an engagement structure 1550 as follows.

Referring to FIGS. 22 and 23, the engagement structure 1550 includes one or more rails and one or more electrical contacts 1560 exposed on the outer surface of the rails. In a certain embodiment, the engagement structure 1550 includes a first rail 1552 and a second rail 1554 generally extending in a parallel fashion to the first rail 1552. Each rail includes at least one contact such as contact 1560 shown on rail 1554, and contact 1562 shown on an oppositely directed side of rail 1552. The neck 1514 defines a receiving region which, for the structure shown in the referenced figures, includes at least two recesses defined within the neck 1514. Each recess is adapted and sized to receive a rail. Referring to FIG. 23, a corresponding contact can be positioned along the interior wall of the receiving region such that when the head 1516 is engaged on the neck 1514 of the toothbrush, the respective contact pads are placed in electrical communication with each other. Specifically, FIG. 23 illustrates a contact 1570 and a contact 1572. The contact 1570 is positioned within the receiving region such that upon engagement of the toothbrush head 1516 on the neck 1514, the contacts 1560 and 1570 are placed in electrical communication with each other. Similarly, the contact 1572 is positioned and located within the receiving region for the other rail such that upon installation of the head to the neck, the contact 1562 is placed in electrical communication with the contact 1572. It is contemplated that one or more of the contacts can be mounted on outwardly projecting pads or biasing members to further promote electrical communication with a corresponding contact.

Figure 27:
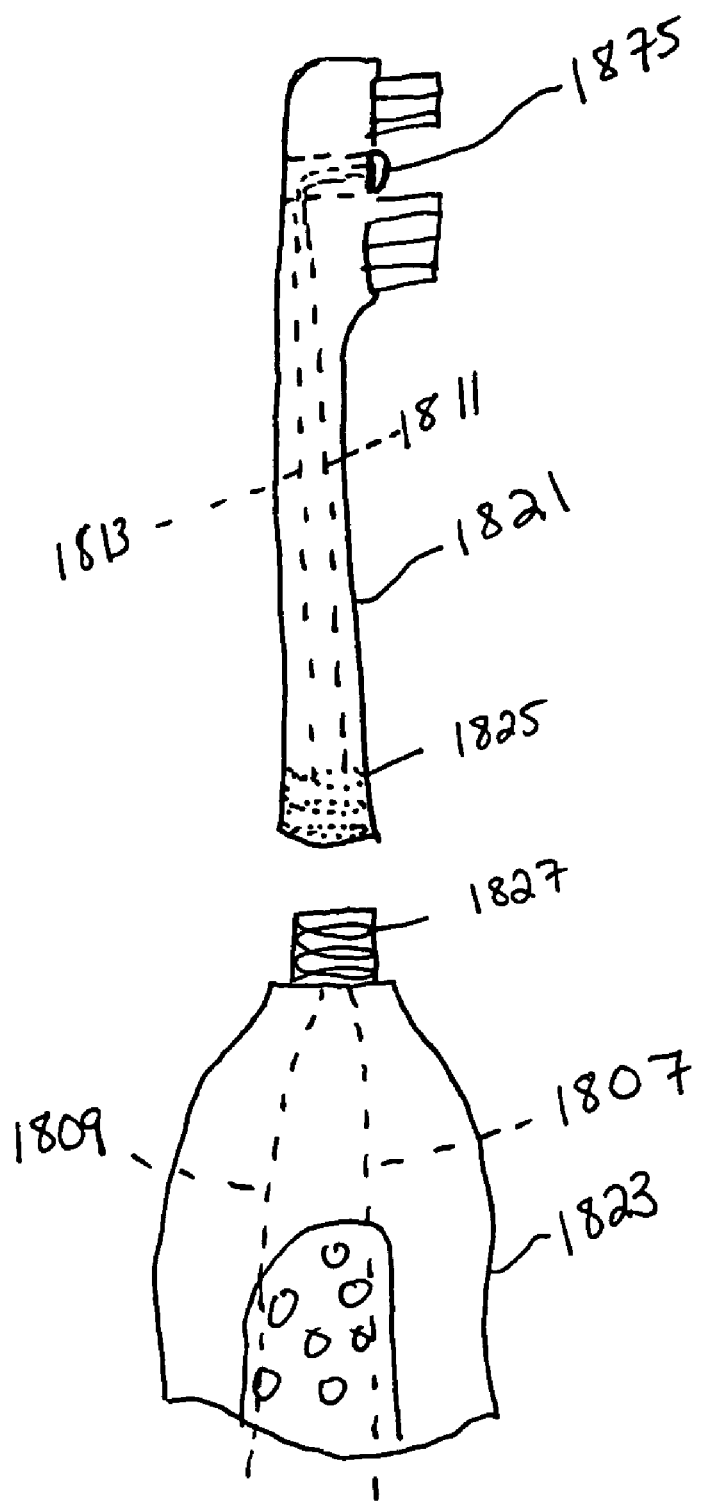
FIG. 27 is a partial view of a toothbrush in accordance with the present invention illustrating an induction connection.
Figures 28, 29:
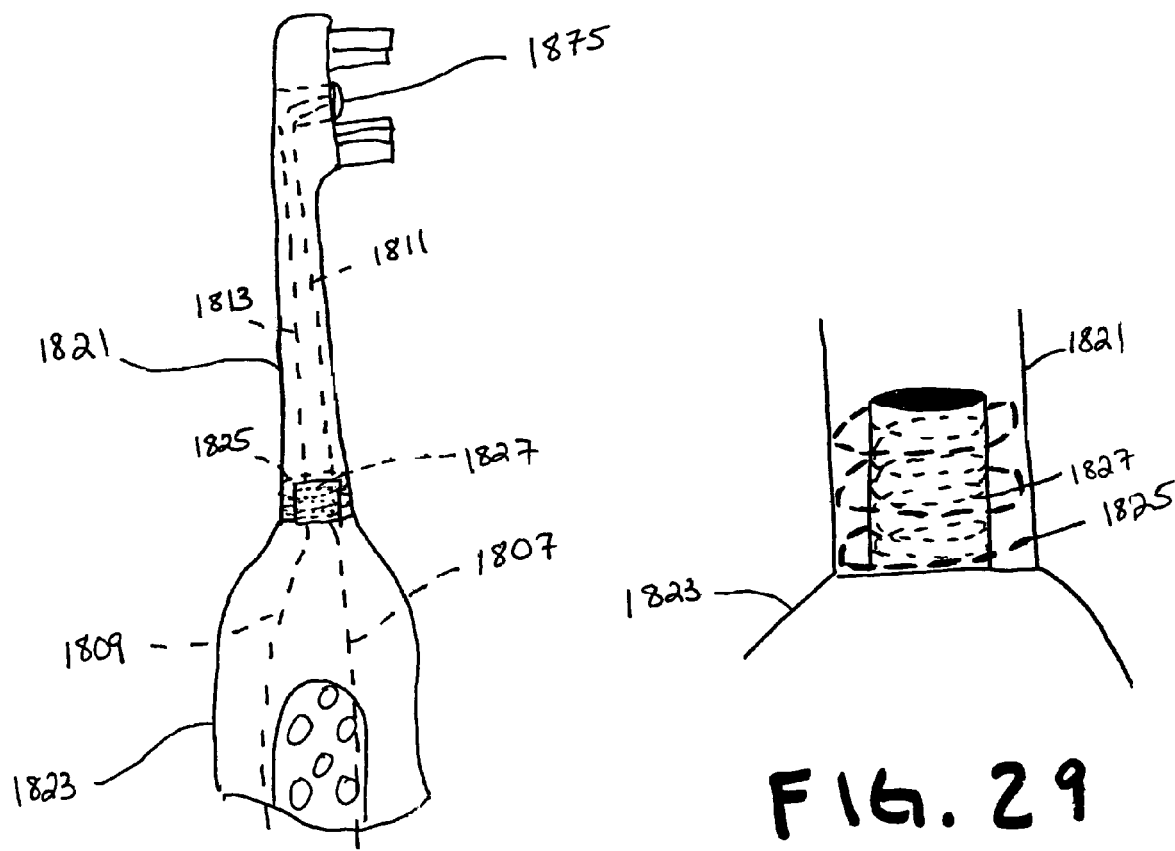
FIG. 28 is a partial view of the toothbrush as shown in FIG. 27 illustrating an induction connection.
FIG. 29 is a partial exploded view of the toothbrush as shown in FIG. 27 illustrating an induction connection.

Additionally, the connector need not include contacts; rather electrical communication between the head and the handle can be established with induction and/or capacitance. An induction connection can transmit electrical power from the handle to the head by the action of magnetic induction (as shown in FIGS. 26-29). FIGS. 27-29 illustrate the handle comprising a primary coil 1800 and the head comprising a secondary coil 1801. The primary coil 1800 fits inside the secondary coil 1801, and the two coils are magnetically coupled. Once the two coils are magnetically coupled the electric power is transferred from the primary coil to the secondary coil. The primary coil 1800 can be mechanically connected to a power supply, such as battery 1803 by leads 1807 and 1809. The power circuit comprises the primary coil 1800, the battery 1803, the motor 1805, and a DC to AC converter. Electric communication between the secondary coil 1801 and the LED 1875 also can be mechanical, the secondary coil 1801 and LED 1875 can be connected by leads 1811 and 1813. The induction connection can also be established by a primary coil 1800, a secondary coil 1801 and a ferromagnetic core 1819 which extends between both coils (as in embodiment 1815 shown in FIG. 26). This ferromagnetic core 1819 magnetically connects the primary coil 1800 to the secondary coil 1801, thereby transferring electric power from the primary coil to the secondary coil and powering the electric element, such as LED 1875, disposed on the head of the toothbrush. A rectifier can be provided in the head portion of the brush if the electrical element disposed on the head needs the energy to be converted into DC form. Alternatively, if the electrical element disposed on the head is an LED, the LED itself can be used as a rectifier due to its electrical diode characteristics.

Figure 30:
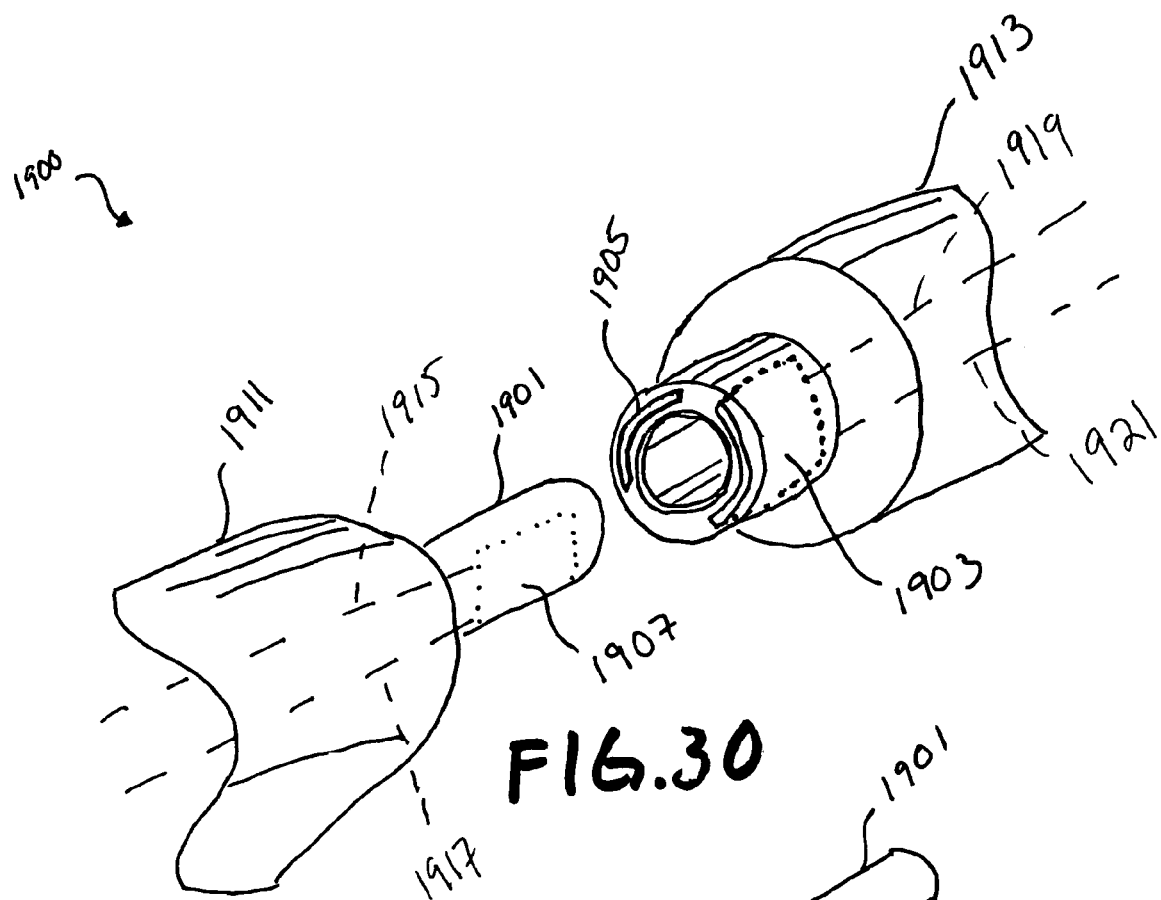
FIG. 30 is a partial view of a toothbrush in accordance with the present invention illustrating a capacitance connection.
Figure 31:
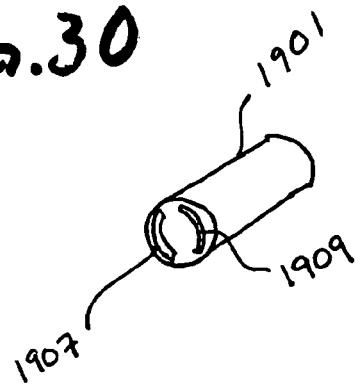
FIG. 31 is a partial exploded view of the toothbrush as shown in FIG. 30 illustrating the capacitance connection.

Electrical power can also be delivered to the element disposed on the head of the toothbrush 1900 via a capacitance connection (as shown in FIGS. 30-31). To achieve electrical communication between the head and the handle with capacitance the electrical connector includes at least two pieces of conductors disposed at a distance apart, one piece of conductor 1907 having a positive charge, and the other piece of conductor 1903 having a negative charge; thereby forming a capacitor. The two pieces of conductor can be placed at the desired distance apart to form a capacitor when the removable head 1911 of the toothbrush engages the handle 1913 of the toothbrush 1900. Once a capacitor is formed, alternating the charge in the first piece of conductor can cause alternating of the charge in the second piece of conductor, because these pieces are bound by the electric field. This way, the capacitor can conduct alternating electric current. By the use of this alternating electric current, the electrical power can be delivered from the handle portion of the electric toothbrush to the head portion. One capacitor formed by two conductive pieces can replace a single pair of regular electrical contacts. Therefore, if two pairs of electrical contacts are desired, a second set of conductors are also desired to form a second capacitor, one piece of conductor 1909, and a second piece 1905. Piece of conductor 1907 can be connected to the positive lead 1917 of the electrical element (not shown) disposed on the head 1911 of the toothbrush 1900. Piece of conductor 1909 can be connected to the negative lead 1915 of the electrical element (not shown) disposed on the head 1911 of the toothbrush 1900. Piece of conductor 1905 can ultimately be connected to the negative pole 1919 of the battery; and piece of conductor 1903 can ultimately be connected to positive pole 1921 of the battery. However, a DC to AC converter can be placed in the circuit between the battery and the pieces of capacitor to convert DC to AC. A rectifier can be provided in the head portion of the brush to which the capacitor is connected if the electrical element disposed on the head needs the energy to be converted into DC form. Alternatively, if the electrical element disposed on the head is an LED, the LED itself can be used as a rectifier due to its electrical diode characteristics.

As previously noted, the present invention toothbrush can include one or more wiping elements to facilitate or promote electrical communication across components of the connector. This element may be considered a flexible lip exclusion seal. The wiping elements are positioned proximate the one or more components of the connector such that upon engaging the head to the neck, the wiping element wipes or brushes across the surface of one or more components of the connector thereby wiping debris and/or moisture from the surface of the one or more components. Specifically, shown in FIG. 23, a plurality of wiping elements are provided as follows. A wiping element 1582 is positioned and defined within the interior region of the neck 1514 such that as the head 1516 is moved into engagement with the neck 1514, the wiping element 1582 wipes over the surface of the component of the connector, such as contact 1562. Similarly, another wiping element 1588 is defined within the receiving region such that upon engagement of the toothbrush head 1516 with the neck 1514, the wiping element 1588 wipes or brushes across the face of contact 1560. If additional components of the connector are provided on other surfaces of the rails such as on the inwardly facing surfaces of the two rails, additional wiping elements such as 1584 and 1586 can be provided. As will be understood, the wiping element can be disposed at any region, or on any portion of the present invention toothbrushes. For instance, the wiping element can be disposed on the head, the neck, the handle, or on any combination of these. Additionally, the electrical connector components can serve as wipers. If the connector components are joined via a sliding movement, and the connector components comprise a flexible material, the components themselves can act to wipe off the area of the connector component. In particular if the embodiment of the inventive toothbrush uses a L-shaped slot (as shown in FIGS. 12-13) or a receiving portion to connect the head to the body of the toothbrush, and the components of the connectors comprise a flexible material, the components of the connectors can act as a wiping element, and wipe off the surface of the connector component during the turning motion to lock the head into place. This press and twist action of the L-shaped slot allows the components of the connectors to wipe and remove any water or other material existing in the area so that the electrical connection can be made without interference.

Figure 24:
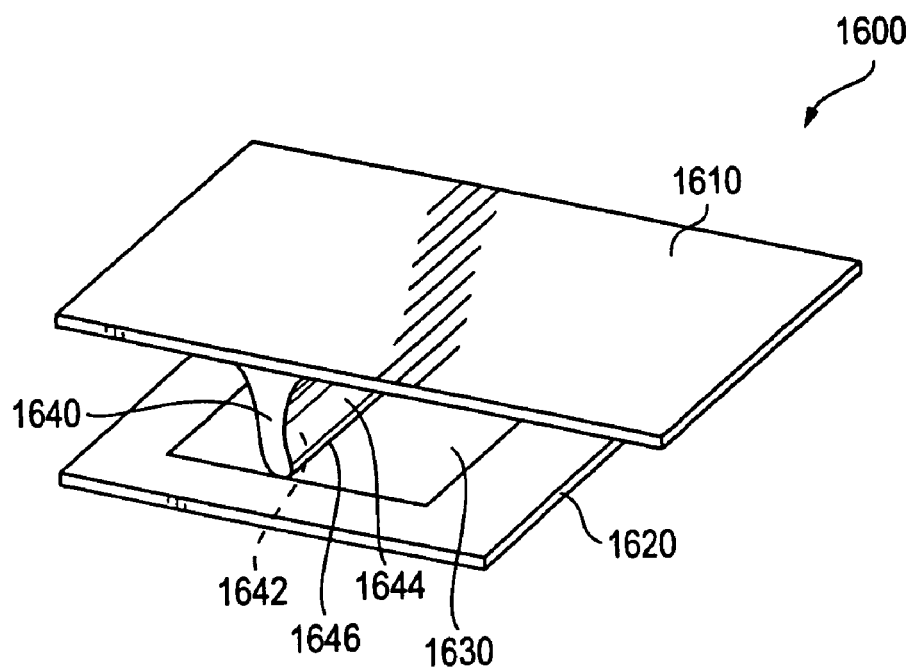
FIG. 24 is a perspective view of a wiping element and connector in accordance with the present invention.

FIG. 24 illustrates in greater detail the wiping engagement or positioning of a wiping element. Specifically, in FIG. 24, a wiping assembly 1600 is illustrated featuring a first substrate 1610 having a flexible yet resilient wiping element 1640 projecting outwardly therefrom. The assembly 1600 also includes a substrate 1620 which includes an electrical connector component such as contact 1630. The wiping element 1640 includes a first face 1644 and a second, oppositely directed face 1642. The two faces 1642 and 1644 extend from the substrate 1610 down to a point or line of convergence 1646. This is also referred to herein as the tip of the wiping element, such as tip 1646 of wiping element 1640. It will be appreciated that as the two substrates 1610 and 1620 are moved past one another, the outwardly directed face of the contact 1630 is moved past and in contact with the tip 1646 of the wiping element 1640. The elastomeric and flexible nature of the wiping element such as wiping element 1640 enables that element to bend or flex depending upon the proximity and engagement with the electrical contact 1630.

Figure 25:
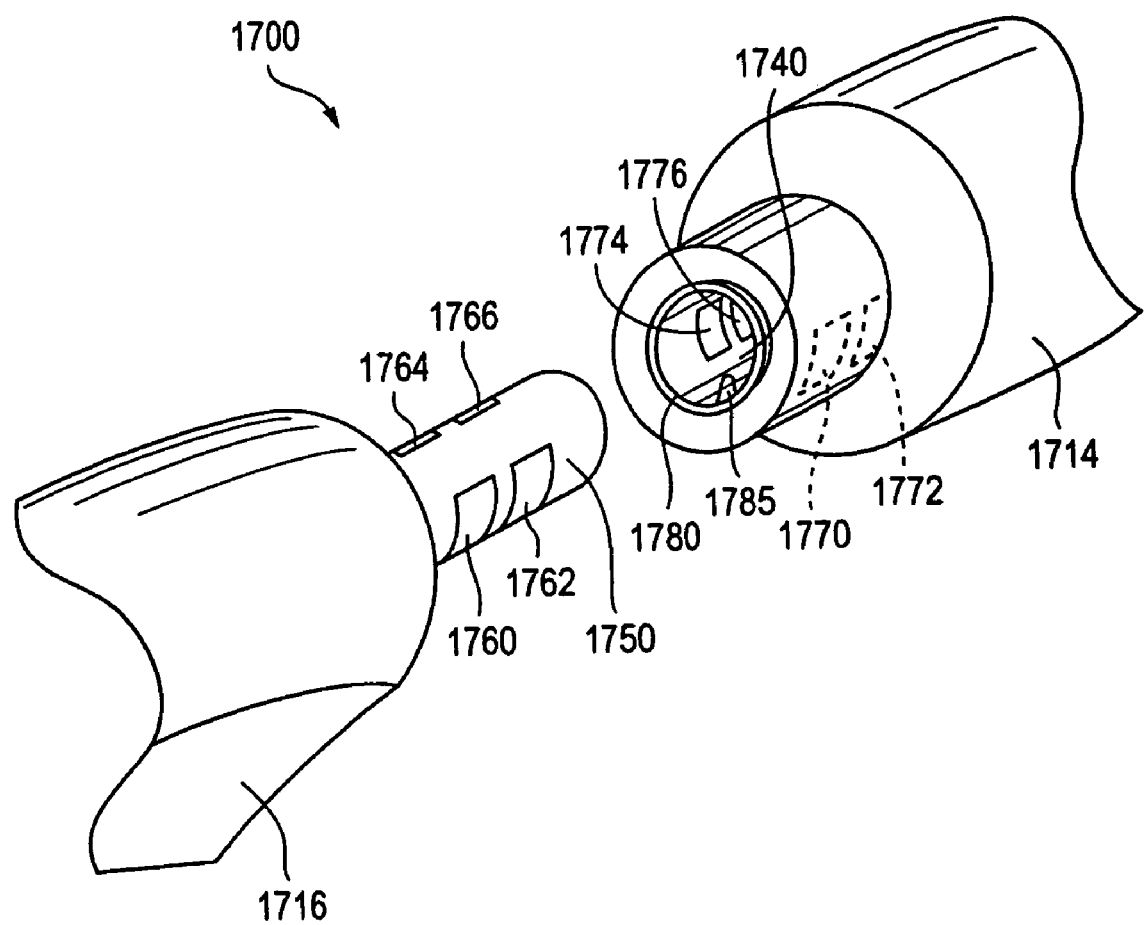
FIG. 25 is a partial sectional of the toothbrush illustrating engagement of the head and neck portions.
Figure 26:
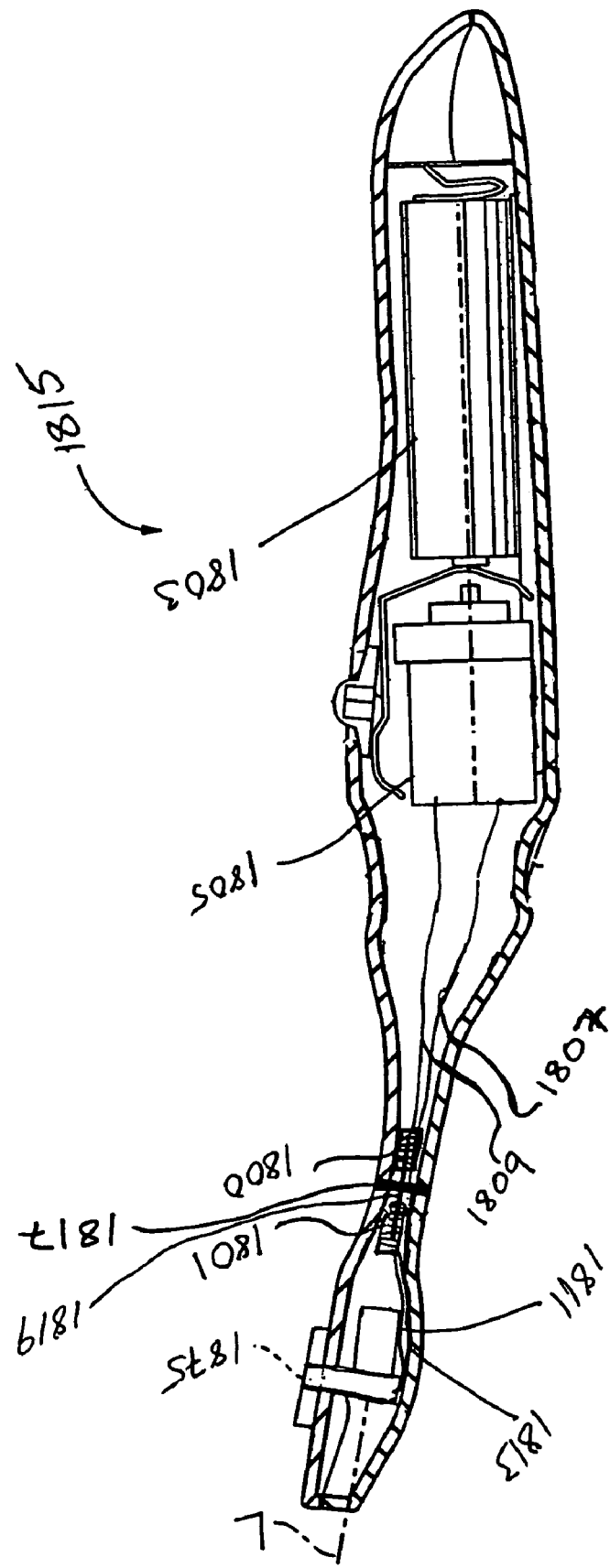
FIG. 26 is a cross sectional view of a toothbrush in accordance with the present invention illustrating an induction connection.

FIG. 25 illustrates another toothbrush according to the present invention. Specifically, FIG. 25 illustrates a toothbrush 1700 comprising a neck 1714 extending from a handle (not shown) which engages with a removable head 1716 as described herein. Extending from an end of the head 1716 is an engagement member 1750. The engagement member 1750 is generally in the form of a cylinder. Positioned along the exterior circumferential surface of the cylinder are a plurality of contacts. In the representative embodiment shown in FIG. 25, a first set of electrical contacts 1760 and 1762 are provided on one side or region of the engagement member 1750, and a second set of electrical contacts 1764 and 1766 are provided on the other, opposite side or region of the member 1750. The neck defines a receiving region 1740 which is sized and adapted to engage and retain the member 1750 of the head 1716. The receiving region 1740 is generally in the configuration of a hollow tubular region. Provided near the opening of the receiving region 1740 is an alignment member 1785. It may in certain applications be beneficial to provide a groove along a portion of the engagement member 1750 which can accommodate the alignment member 1785 upon engagement of the head 1716 to the neck 1714. The function of the alignment member 1785 is described below. Defined along the interior surface of the receiving region 1740 are a plurality of electrodes. Specifically, electrodes 1770 and 1772 are provided on one area or portion of the receiving region 1740, and another set of electrodes 1774 and 1776 are provided on an opposite region. The electrodes 1770 and 1772 are aligned and positioned within the receiving region 1740 such that upon engagement of the head 1716 with the neck 1714, the contact 1770 and 1772 are placed in electrical communication with the corresponding electrical contacts 1760 and 1762, respectively. Similarly, the electrodes 1774 and 1776 are positioned along the interior of the receiving region 1740 such that upon engagement of the head 1716 to the neck 1714, the contacts 1774 and 1776 are placed in electrical communication with the contacts 1764 and 1766, respectively, on the engagement member 1750. As will be appreciated by those skilled in the art, one or more electrical circuits will be established upon electrical communication between the corresponding sets of contacts. In order to ensure that proper electrical communication is made between corresponding contacts, the alignment member 1785 ensures proper orientation of the head 1716 with the neck 1714. As previously noted, a groove or channel or other recessed region (not shown) is provided along the engagement member 1750 which receives and accommodates the alignment member 1785 upon engagement of the head 1716 to the neck 1714.

In the embodiment illustrated in FIG. 25, a circular wiping element 1780 is also illustrated. The wiping element 1780 is, in this particular embodiment, in the form of an O-ring. The wiping element 1780 is sized such that it wipes and contacts the exposed faces of at least one or more of the contacts 1760, 1762, 1764, and 1766 upon engagement of the head 1716 to the neck 1714.

FIG. 25*a-b* illustrate another embodiment of the toothbrush made according to the present invention. This embodiment of the toothbrush has spring biased contacts 1792 and 1793 which must be pushed down into the brush head to complete the connection. When the head 1791 engages the handle 1790 of the toothbrush, contacts 1795 and 1794 push spring biased contacts 1792 and 1793 down into the handle of the brush, where these contacts meet wires which are connected to the power source (not shown) and the electrical connection is complete. The head or the handle of the toothbrush can also comprise a polymer layer 1796 which is compressible. When the head engages the handle of the toothbrush this layer compresses and acts as a seal. If the head engages the handle by pressing the head onto the handle and then twisting the head to align the toothbrush (as shown in FIGS. 12 and 13) this compressible polymer layer 1796 can be a wiping element, wiping off the contacts and removing any water from the contact area. Further this compressible polymer layer 1796 can be a seal, preventing water from entering the interior of the toothbrush. It is contemplated that this compressive polymer layer can also be disposed on the head portion of the toothbrush.

The wiping elements can be formed from a variety of materials, such as but not limited to, ethylene acrylic, ethylene propylene diene monomer (EPDM), fluoroelastomer, fluorosilicone, nitrile rubber (NBR—Buna-N), nitrile highly saturated rubber (HNBR), nylon/polyamide, polyacrylates, polychloroprene (Neoprene), polyetheretherketone (PEEK), polyoxymethylenes, polytetrafluoroethylene (PTFE—Teflon®), polyurethane/urethane, natural rubber (NR), and combinations thereof.

A wide variety of light-emitting elements may be used with the present invention. Generally, the light-emitting element is a small, low power consumption, light emitting diode (LED) such as those commercially available under the designation Luxeon™ manufactured by Lumileds Lighting, LLC of San Jose Calif. Other commercially available light-emitting units include those from American Opto Plus LED Corporation. The LED operates from a relatively low voltage DC power supply, such as between about 0.5 volt and about 5 volts, generally between about 1 volt and 3 volts, and typically from about 1.6 to about 2.4 volts.

The various toothbrushes described herein may utilize light-emitting elements having a variety of characteristics. Concerning wave length, the light-emitting elements used in the toothbrushes described herein emit light having a centroid wave length between about 10 nm and about $10^6$ nm, generally between about 370 nm to about 770 nm, typically from about 420 nm to about 490 nm, and for a blue light often between about 430 nm and about 480 nm. It will be appreciated that the particular range of wavelengths selected depend upon the desired color of the light. Since it is believed that blue light can enhance the bleaching of teeth, light-emitting elements that have a centroid wavelength within the blue spectrum can be utilized.

Figure 14:
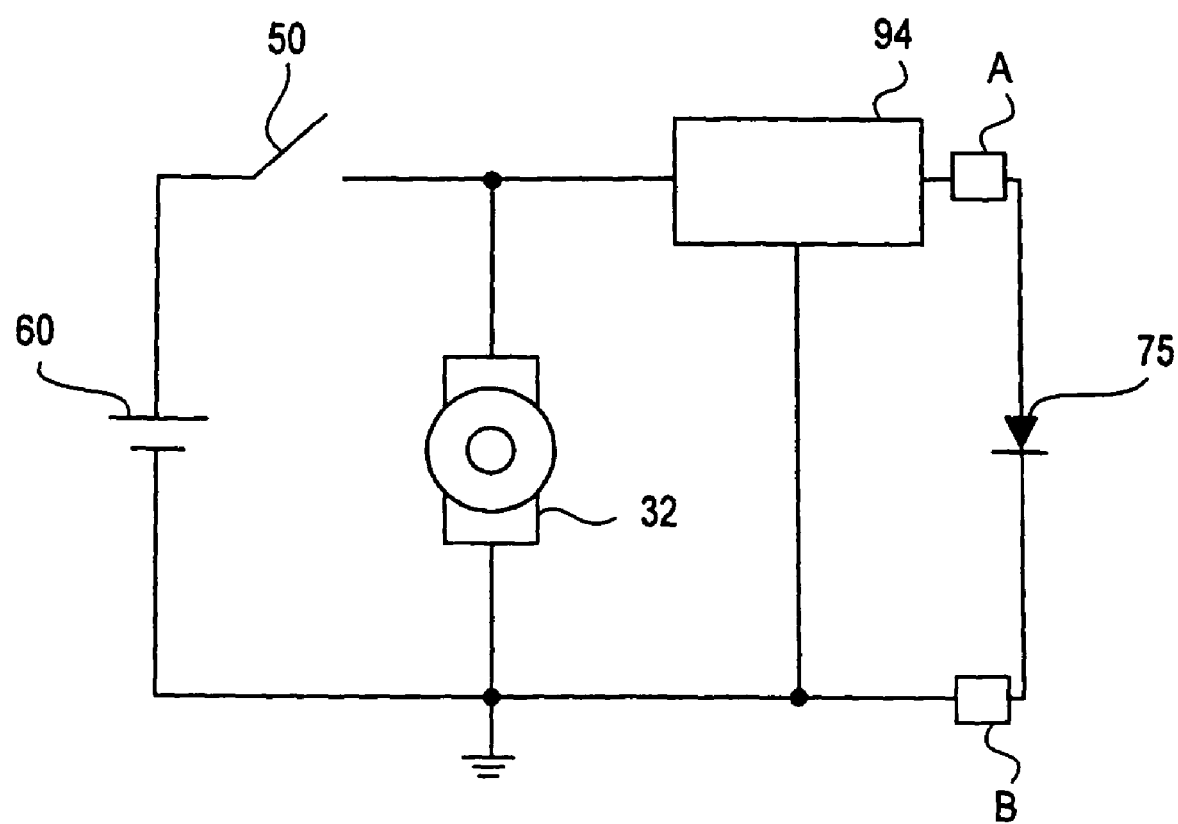
FIG. 14 is a schematic of an electrical configuration suitable for use with the present invention.

FIG. 14 illustrates one possible schematic of an electrical configuration for the present invention toothbrushes. In this configuration, the light-emitting element 75 and the motor 32 are powered or activated concurrently with one another by switch 50, such as shown for example in FIGS. 1-4. When the light-emitting element 75 is an LED, it may be desirable to include a voltage or current driver 94 which provides a constant voltage or current output to the LED despite changes to the input voltage or current, especially as the voltage or current output from a battery tends to decrease over time. A voltage or current driver suitable for use with the present invention is the ZXSC310 Single or Multi Cell LED Driver manufactured by Zetex Semiconductors, Oldham, UK. While the schematic shown in FIG. 14 is illustrated, other configurations can be provided. For example, separate switches might be provided to separately active the light-emitting element and the motor. More than one light-emitting element might be provided. Light-emitting elements having different spectral, photometric, radiometric, and colormeteric characteristics (e.g., different dominant wavelengths, peak wavelengths, radiometric power, etc.) might be provided to accommodate multiple uses in a single electric toothbrush (i.e., the first light-emitting element might be adapted for use with a first light activated composition and the second light-emitting element might be adapted for use with a second light-activated composition). The severable electrical contacts described herein are designated as elements A and B in the noted schematic. For example, element A could include a first pair of engageable electrical contacts and element B could include a second pair of engageable electrical contacts, both of which provide for removal and re-incorporation of the element 75 within the circuit as the toothbrush head is removed and/or re-attached to the handle of the toothbrush.

It will be appreciated that in all of the embodiments described herein, typically the connector can comprise four contacts per toothbrush, however, the present invention includes the use of any number of contacts, including four, six, eight or more. If four contacts are present typically two contacts are disposed on the handle and two contacts are disposed on the head. Upon engagement of the head to the handle, the two contacts are placed in electrical communication with each other and continue the electrical path.

The present invention also includes the use of more than one connector, particularly for those applications in which an electrical connection is established for two or more electrically powered elements provided on the brush head. For example, multiple connectors can be used if the electrically powered elements are individually actuated or controlled by switches or controls on the handle of the toothbrush. The present invention further includes the use of multiple power supplies that are individually dedicated to certain electrically powered elements on the head. And, it is further contemplated that multiple electrical circuits could be incorporated in the toothbrushes of the present invention, which would require a greater number of connectors While LEDs are the contemplated light-emitting elements, a wide array of other light configurations, light-emitting elements, and/or other electrical elements may be used in the toothbrushes described herein including, but not limited to, light-emitting units using incandescent elements, laser elements, halogen elements, neon elements, fluorescent elements, plasma elements, xenon elements, flossing elements, massaging elements, scraping elements, heat emitting elements, sonic wave emitting elements, electric current emitting elements, composition emitting elements and/or combinations thereof.

The housing and the brush head may be formed from a wide array of polymers. In the following description of the polymer materials for use herein, the abbreviations that are commonly used by those of skill in the art to refer to certain polymers appear in parentheses following the full names of the polymers. The polymer can be for example polypropylene ("PP"), or may be selected from the group consisting of other commercially available materials, such as polystyrene ("PS"), polyethylene ("PE"), acrylonitrile-styrene copolymer ("SAN"), and cellulose acetate propionate ("CAP"). These materials may be blended with one or more additional polymers including a thermoplastic elastomer ("TPE"), a thermoplastic olefin ("TPO"), a soft thermoplastic polyolefin (e.g., polybutylene), or may be selected from other elastomeric materials, such as ethylene-vinylacetate copolymer ("EVA"), and ethylene propylene rubber ("EPR"). Examples of suitable thermoplastic elastomers herein include styrene-ethylene-butadiene-styrene ("SEBS"), styrene-butadiene-styrene ("SBS"), and styrene-isoprene-styrene ("SIS"). Examples of suitable thermoplastic olefins herein include polybutylene ("PS"), and polyethylene ("PE").

Techniques known to those of skill in the art, such as injection molding, can be used to manufacture the toothbrushes of the present invention.

The present invention has been described with reference to various embodiments. Obviously, modifications and alterations will occur to others upon a reading and understanding of this specification. For example, any number of bristle holders and bristle patterns can be utilized with the present invention along with one more light-emitting elements. Further, any and all aspects or features can be combined with any and all other aspects or features of the noted embodiments. The present invention is intended to include all such modifications and alterations insofar as they come within the scope of the appended claims or the equivalents thereof.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric oral care implement for use in the mouth comprising:
    (a) a handle defining a hollow interior region having a battery disposed therein, the handle having an end portion configured to receive the head assembly, the end portion comprising a receiving region;
    (b) a head assembly that is removable from and attachable to said handle, said head assembly comprising at least one electrically powered element and a projection member configured to engage the receiving region, thereby providing mechanical interlock between said head assembly and said handle;
    (c) at least one electrical connector; wherein said at least one electrical connector provides electrical communication between said electrically powered element and said handle upon attachment of said head assembly to said handle, wherein said at least one electrical connector comprises the projection member and the receiving region; and
    (d) a connector wiping element.

2. The electric oral care implement of claim 1, wherein said electric oral care implement is an electric toothbrush.

3. The electric oral care implement of claim 1, wherein said electrically powered element is a light emitting diode.

4. The electric oral care implement of claim 1 further comprising a second electrical connector with a first electrical contact adjacent to the head assembly and a second electrical contact located adjacent to the end portion the second electrical connector being configured to provide electrical communication when the head assembly is attached to the handle.

5. The electric oral care implement of claim 1, wherein said electrically powered element is a wave element.

6. The electric oral care implement of claim 5, wherein said wave element is a sonic wave element.

7. The electrical oral care implement of claim 1, wherein the electrical connector is the projection member and the receiving region.

8. An electric toothbrush, comprising a head portion, a connector wiping element, and a handle portion where said head portion connects to said handle portion, said handle portion having a first portion of an electrical connector, said head portion comprising:
    (a) an electrically powered element; and
    (b) a second portion of said electrical connector; wherein electrical communication between said head portion and said electrically powered element is provided when said head portion engages said handle portion, and wherein mechanical interlock is provided by said first portion and said second portion when engaged;
    (c) a moving bristle holder; and
    (d) a static bristle holder.

9. An electric toothbrush comprising:
    (a) a handle defining a hollow interior region;
    (b) a head and neck assembly that is removable from and attachable to said handle, said head and neck assembly comprising at least one electrically powered element;
    (c) an electrical connector comprising at least a first set of severable electrically conducting contacts, wherein said contacts provide electrical communication between said head and neck assembly and said handle upon attachment of said head and neck assembly to said handle, and wherein said contacts provide mechanical interlock between said head and neck assembly and said handle; and
    (d) a connector wiping element.

* * * * *